(12) United States Patent
Riftine

(10) Patent No.: US 7,826,892 B2
(45) Date of Patent: Nov. 2, 2010

(54) METHOD FOR QUANTITATIVE ASSESSMENT OF THE AUTONOMIC NERVOUS SYSTEM BASED ON HEART RATE VARIABILITY ANALYSIS

(75) Inventor: Alexander Riftine, Brooklyn, NY (US)

(73) Assignee: Intelwave, LLC, Edison, NJ (US)

( * ) Notice: Subject to any disclaimer, the term of this patent is extended or adjusted under 35 U.S.C. 154(b) by 614 days.

(21) Appl. No.: 11/824,869

(22) Filed: Jun. 29, 2007

(65) Prior Publication Data

US 2009/0005696 A1 Jan. 1, 2009

(51) Int. Cl.
A61B 5/04 (2006.01)
(52) U.S. Cl. ...................................... 600/509
(58) Field of Classification Search .............. 607/509, 607/519, 521, 523
See application file for complete search history.

(56) References Cited

U.S. PATENT DOCUMENTS

| | | | |
|---|---|---|---|
| 5,755,671 A * | 5/1998 | Albrecht et al. ............. | 600/516 |
| 6,491,639 B1 | 12/2002 | Turcott | |
| 2005/0143668 A1 | 6/2005 | Lu et al. | |

OTHER PUBLICATIONS

A. Riftine, Quantitative Assessment of the Autonomic Nervous System based on Heart Rate Variability Analysis: Theoretical Review and CLinical Use, Intellewave, LLC (c)2005-2007.*

E. Kazin, A. Riftine. "Automated systems for the complex evaluation of the health and adaptive reserves of the human body." Human Physiology, USSR, 1990, 16(3): 94-99.
M. Minsky. A Framework for Representing Knowledge. MIT-AI Laboratory Memo 306, Jun. 1974.
Riftine, Alexander. Clinical Applications and Practical use of Fully Automatic System for Quantitative Assessment of Autonomic Nervous System Condition Based on Heart rate variability Analysis. In Proceedings of the 18th Annual International Symposium on Man and His Environment in Health and Disease. Special focus: Environmental Aspects of Cardiovascular Disease. Dallas, TX, Jun. 2000.
Riftine, Alexander. ANS Assessment as an Indicator of Environmental Pollution Impacts on the Human Body. In Proceedings of the 23rd Annual International Symposium on Man and His Environment in Health and Disease. Special focus: The Autonomic Nervous System and Its Relationship to Environmental Pollutants Including the Cardiovascular System and Electromagnetic Sensitivity. Dallas, TX, Jun. 2005.

(Continued)

*Primary Examiner*—Carl H Layno
*Assistant Examiner*—Brian T Gedeon
(74) *Attorney, Agent, or Firm*—Gary J. Gershik; Cooper & Dunham LLP

(57) ABSTRACT

A method is provided for characterizing autonomic nervous system activity of a patient based on heart rate variability analysis using electrocardiographic data from the patient. In addition, a computer-readable medium is provided tangibly embodying a program of instructions executable by a computer to perform a method for characterizing autonomic nervous system activity of a patient based on heart rate variability analysis using electrocardiographic data from the patient. Also, a system is provided for characterizing autonomic nervous system activity of a patient comprising a processor and a machine-readable medium tangibly embodying a program of instructions executable by the processor.

11 Claims, 35 Drawing Sheets

OTHER PUBLICATIONS

Riftine, Alexander. Clusterization of the Relationship between SNS and PSNS activity by Heart Rate Variability Analysis. In Proceedings of the 33rd International Congress of Electrocardiology. Cologne, Germany, Jul. 2006.

N. Rottman, C. Steinman, P. Albrecht, T. Bigger, M. Rolnitzky, L. Fleiss. "Efficient estimation of the heart period power spectrum suitable for physiologic or pharmacologic studies." The American Journal of Cardiology, 1990, 66:1522-1524.

Terechtchenko, Larissa, Doronina, Svetlana, Pochinok, Elena and Riftine, Alexander. "Autonomic Tone in Patients with Supraventricular Arrhythmia Associated with Mitral Valve Prolapse in Young Men." Pacing and Clinical Electrophysiology. Jan. 2003, 26: 444-446.

"Heart rate variability. Standards of measurement, physiologic interpretation, and clinical use. Task Force of the European Society of Cardiology and the North American Society of Pacing and Electrophysiology." European Heart Journal, 1996, 17: 354-381.

Oct. 10, 2008 Search Report from counterpart PCT International Application PCT/US2008/07382.

Oct. 10, 2008 Written Opinion of the International Searching Authority.

* cited by examiner

METHOD FOR QUANTITATIVE ASSESSMENT OF THE AUTONOMIC NERVOUS SYSTEM BASED ON HEART RATE VARIABILITY ANALYSIS

BACKGROUND OF THE INVENTION

Heart Rate Variability analysis is based on measuring variations in length of intervals between consecutive R waves further referred to as RR intervals; it usually employs spectral or some other form of mathematical analysis for characterizing such variations. The clinical significance of heart rate variability analysis became apparent when decreased variability of heart rate was found to correlate with certain health abnormalities, e.g. diabetic autonomic neuropathy, myocardial dysfunction etc. (T. Bigger, N. Rottman. Spectral Analysis of RR Variability. Chapter 19 in Cardiac Arrhythmia—Mechanisms, Diagnosis, and Management, Podrid P J, Kowey P R editors. Baltimore: William & Wilkins, 1995: 280-298.) Further studies have established that the high frequency component correlates with the activity of the parasympathetic nervous system while the low frequency component can serve as a marker of both vagal and sympathetic modulation ("Heart rate variability. Standards of measurement, physiologic interpretation, and clinical use. Task Force of the European Society of Cardiology and the North American Society of Pacing and Electrophysiology", European Heart Journal, 1996, 17: 354-381.)

The discovery of such markers of autonomic activity opened up new opportunities of physiologic assessment for a wide range of clinical applications. However, in order to make practical use of this important scientific discovery, it was necessary to solve the problem of deriving some form of quantitative relationship between sympathetic and parasympathetic activity from the spectral function. Mathematical analysis of heart rate variability usually generates multiple parameters, typically 20-30 parameters. Prior methods have typically used two or three parameters of spectral function, such as high frequency power, low frequency power, or ratio of low frequency to high frequency power, and used direct meanings of these parameters for identification of the activities of the parasympathetic nervous system (PSNS) and the sympathetic nervous system (SNS). The remaining parameters were typically not taken into consideration. Thus the problem of SNS-PSNS quantification, which has remained for many years the principal dilemma of HRV analysis, has been specifically in deriving two final parameters: SNS and PSNS, from all the multiple parameters obtained via mathematical analysis of heart rate variability (HRV).

SUMMARY OF INVENTION

In an embodiment a method for characterizing autonomic nervous system activity of a patient is disclosed comprising:
(a) acquiring electrocardiographic data from the patient;
(b) determining from the electrocardiographic data obtained in step (a) a plurality of time intervals between successive R-waves;
(c) analyzing the plurality of time intervals by frequency domain analysis so as to quantitate the following parameters:
   i) power of high frequency (PHF);
   ii) power of low frequency 1 (PLF1);
   iii) power of low frequency 2 (PLF2);
   iv) difference between power of low frequency 1 and high frequency (PLF1-PHF);
   v) maximum amplitude of spectral function in a low frequency band (SLFmax);
   vi) frequency at a point of maximum amplitude of spectral function in the low frequency band (FLFmax);
   vii) maximum amplitude of spectral function in a high frequency band (SHFmax);
   viii) frequency at a point of maximum amplitude of spectral function in the high frequency band (FHFmax);
   ix) ratio of power of high frequency to power of low frequency 1, (PHF/PLF1);
   x) ratio of power of high frequency to power of low frequency (sum of powers of low frequency 1 and low frequency 2), (PHF/(PLF1+PLF2));
   xi) heart rate (HR);
   and, if a spectral peak falls in the range of a middle frequency band,
   xii) (SMF) maximum amplitude of spectral function in a middle frequency band; and
(d) applying an clusterization algorithm to the parameter values quantitated in step (c) so as to determine two further parameters, one of which correlates with sympathetic nervous system activity and the other of which correlates with parasympathetic nervous system activity, so as to thereby characterize the autonomic nervous system activity of the patient.

In an embodiment a computer-readable medium tangibly embodying a program of instructions executable by a computer to perform a method for characterizing autonomic nervous system activity of a patient is disclosed which method comprises:
(a) acquiring electrocardiographic data from the patient;
(b) determining from the electrocardiographic data obtained in step (a) a plurality of time intervals between successive R-waves;
(c) analyzing the plurality of time intervals by frequency domain analysis so as to quantitate the following parameters:
   i) power of high frequency ($P_{HF}$);
   ii) power of low frequency 1 ($P_{LF1}$);
   iii) power of low frequency 2 ($P_{LF2}$);
   iv) difference between power of low frequency 1 and high frequency ($P_{LF1}$ -$P_{HF}$);
   v) maximum amplitude of spectral function in a low frequency band ($S_{LFmax}$);
   vi) frequency at a point of maximum amplitude of spectral function in the low frequency band ($F_{LFmax}$);
   vii) maximum amplitude of spectral function in a high frequency band ($S_{HFmax}$);
   viii) frequency at a point of maximum amplitude of spectral function in the high frequency band ($F_{HFmax}$);
   ix) ratio of power of high frequency to power of low frequency 1, ($P_{HF}/P_{LF1}$);
   x) ratio of power of high frequency to power of low frequency (sum of powers of low frequency 1 and low frequency 2), ($P_{HF}/(P_{LF1}+P_{LF2})$);
   xi) heart rate (HR);
   and, if a spectral peak falls in the range of a middle frequency band,
   xii) ($S_{MF}$) maximum amplitude of spectral function in a middle frequency band; and
(d) applying a clusterization algorithm to the parameter values quantitated in step (c) so as to determine two further parameters, one of which correlates with sympathetic nervous system activity and the other of which correlates with parasympathetic nervous system activity In an embodiment a method for analyzing electrocardiographic data is disclosed comprising:

(a) analyzing a plurality of time intervals between successive R-waves of the electrocardiographic data by frequency domain analysis so as to quantitate the following parameters:
  i) power of high frequency ($P_{HF}$);
  ii) power of low frequency 1 ($P_{LF1}$);
  iii) power of low frequency 2 ($P_{LF2}$);
  iv) difference between power of low frequency 1 and high frequency ($P_{LF1}$-$P_{HF}$);
  v) maximum amplitude of spectral function in a low frequency band ($S_{LFmax}$);
  vi) frequency at a point of maximum amplitude of spectral function in the low frequency band ($F_{LFmax}$);
  vii) maximum amplitude of spectral function in a high frequency band ($S_{HFmax}$);
  viii) frequency at a point of maximum amplitude of spectral function in the high frequency band ($F_{HFmax}$);
  ix) ratio of power of high frequency to power of low frequency 1, ($P_{HF}/P_{LF1}$);
  x) ratio of power of high frequency to power of low frequency (sum of powers of low frequency 1 and low frequency 2), ($P_{HF}/(P_{LF1}+P_{LF2})$);
  xi) heart rate (HR);
  and, if a spectral peak falls in the range of a middle frequency band,
  xii) ($S_{MF}$) maximum amplitude of spectral function in a middle frequency band; and
(b) applying a clusterization algorithm to the parameter values quantitated in step (a) so as to determine two further parameters, one of which correlates with sympathetic nervous system activity and the other of which correlates with parasympathetic nervous system activity.

DETAILED DESCRIPTION OF THE INVENTION

Figure 1:
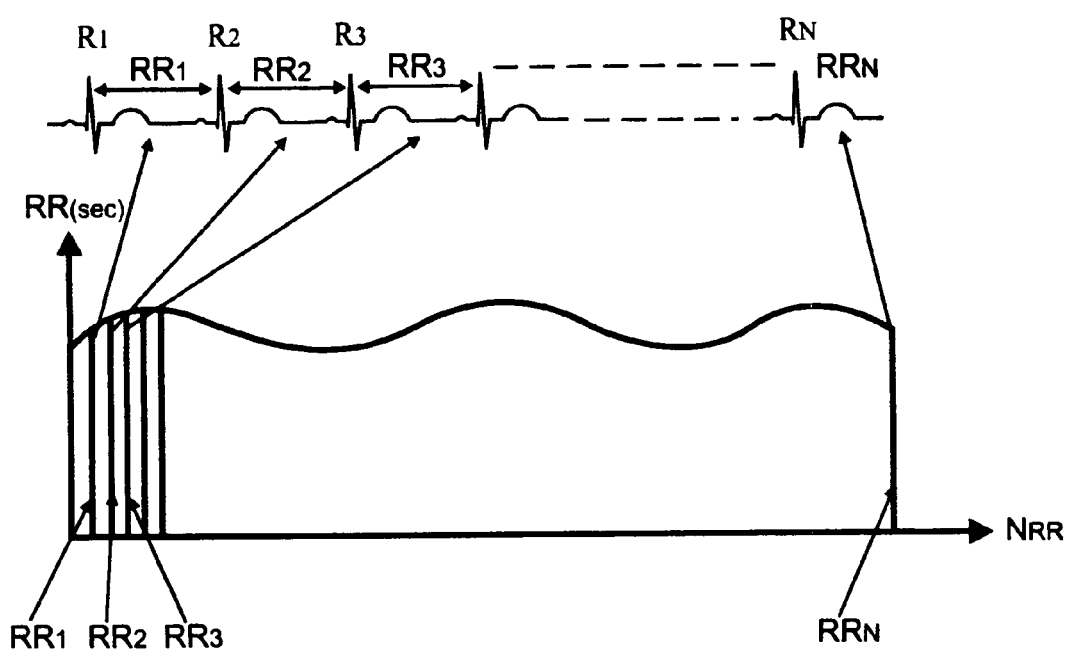
FIG. 1 RR intervals are recorded in a method of rhythmography.

The present invention provides a method for quantitative assessment of the autonomic nervous system (ANS) based on heart rate variability analysis (HRV). This method is referred to herein as "The Intelwave Method". The present invention also encompasses systems for implementing the method.

"Electrocardiographic data" as used herein means information describing the electrical activity of a heart obtained, for example, by an electrocardiograph. In an embodiment, the electrocardiographic data is obtained through recording electrodes placed on a human.

"R-wave" as used herein correlates to the positive voltage spike in an ECG signal coincident with a ventricular contraction.

"Data preparation algorithm" as used herein is the treatment of data to recognize artifacts and ectopic beats and replace them with interpolated values; recognition of patterns of ectopic beats such as bigeminy, trigeminy and quadrigeminy; recognition of ectopic beats such as isolated ventricular extrasystoles, supraventricular extrasystoles interpolated ventricular extrasystoles, and dropped QRS complexes by analyzing 5-6 pairs of adjacent R-R intervals; generation of a histogram of ectopic beat intervals for estimated placement of extrasystoles; analysis of results of the recognition of ectopic beat and artifact patterns, isolated extrasystoles and dropped QRS complexes (QRSdr) for making the internal conclusion about the presence and type of extrasystoles.

"Power spectral analysis algorithm" as used herein shall mean frequency domain analysis, e.g. through Fast Fourier Transform, to characterize fluctuations of RR intervals. The algorithm may additionally include correction of results of power spectral analysis in the presence of abnormal beat signals through the use of frequency subranges in spectral analysis.

"Clusterization algorithm" as used herein shall mean frame aggregate for recognition of (parasympathetic nervous system) PSNS cluster point and frame aggregate for recognition of SNS (sympathetic nervous system) cluster point so as to determine the balance of intensities of PSNS and SNS activities.

In an embodiment a method for characterizing autonomic nervous system activity of a patient is disclosed comprising:
(a) acquiring electrocardiographic data from the patient;
(b) determining from the electrocardiographic data obtained in step (a) a plurality of time intervals between successive R-waves;
(c) analyzing the plurality of time intervals by frequency domain analysis so as to quantitate the following parameters:
 i) power of high frequency ($P_{HF}$);
 ii) power of low frequency 1 ($P_{LF1}$);
 iii) power of low frequency 2 ($P_{LF2}$);
 iv) difference between power of low frequency 1 and high frequency ($P_{LF1}$-$P_{HF}$);
 v) maximum amplitude of spectral function in a low frequency band ($S_{LFmax}$);
 vi) frequency at a point of maximum amplitude of spectral function in the low frequency band ($F_{LFmax}$);
 vii) maximum amplitude of spectral function in a high frequency band ($S_{HFmax}$);
 viii) frequency at a point of maximum amplitude of spectral function in the high frequency band ($F_{HFmax}$);
 ix) ratio of power of high frequency to power of low frequency 1, ($P_{HF}/P_{LF1}$);
 x) ratio of power of high frequency to power of low frequency (sum of powers of low frequency 1 and low frequency 2), ($P_{HF}/(P_{LF1}+P_{LF2})$);
 xi) heart rate (HR);
 and, if a spectral peak falls in the range of a middle frequency band,
 xii) ($S_{MF}$) maximum amplitude of spectral function in a middle frequency band; and
(d) applying an clusterization algorithm to the parameter values quantitated in step (c) so as to determine two further parameters, one of which correlates with sympathetic nervous system activity and the other of which correlates with parasympathetic nervous system activity, so as to thereby characterize the autonomic nervous system activity of the patient.

In an embodiment a computer-readable medium tangibly embodying a program of instructions executable by a computer to perform a method for characterizing autonomic nervous system activity of a patient is disclosed which method comprises:
(a) acquiring electrocardiographic data from the patient;
(b) determining from the electrocardiographic data obtained in step (a) a plurality of time intervals between successive R-waves;
(c) analyzing the plurality of time intervals by frequency domain analysis so as to quantitate the following parameters:
 i) power of high frequency ($P_{HF}$);
 ii) power of low frequency 1 ($P_{LF1}$);
 iii) power of low frequency 2 ($P_{LF2}$);
 iv) difference between power of low frequency 1 and high frequency ($P_{LF1}$-$P_{HF}$);
 v) maximum amplitude of spectral function in a low frequency band ($S_{LFmax}$);
 vi) frequency at a point of maximum amplitude of spectral function in the low frequency band ($F_{LFmax}$);
 vii) maximum amplitude of spectral function in a high frequency band ($S_{HFmax}$);
 viii) frequency at a point of maximum amplitude of spectral function in the high frequency band ($F_{HFmax}$);
 ix) ratio of power of high frequency to power of low frequency 1, ($P_{HF}/P_{LF1}$);
 x) ratio of power of high frequency to power of low frequency (sum of powers of low frequency 1 and low frequency 2), ($P_{HF}/(P_{LF1}+P_{LF2})$);
 xi) heart rate (HR);

and, if a spectral peak falls in the range of a middle frequency band,
 xii) ($S_{MF}$) maximum amplitude of spectral function in a middle frequency band; and
(d) applying a clusterization algorithm to the parameter values quantitated in step (c) so as to determine two further parameters, one of which correlates with sympathetic nervous system activity and the other of which correlates with parasympathetic nervous system activity In an embodiment a method for analyzing electrocardiographic data is disclosed comprising:
(a) analyzing a plurality of time intervals between successive R-waves of the electrocardiographic data by frequency domain analysis so as to quantitate the following parameters:
 i) power of high frequency ($P_{HF}$);

ii) power of low frequency 1 ($P_{LF1}$);
iii) power of low frequency 2 ($P_{LF2}$);
iv) difference between power of low frequency 1 and high frequency ($P_{LF1}$-$P_{HF}$);
v) maximum amplitude of spectral function in a low frequency band ($S_{LFmax}$);
vi) frequency at a point of maximum amplitude of spectral function in the low frequency band ($F_{LFmax}$);
vii) maximum amplitude of spectral function in a high frequency band ($S_{HFmax}$);
viii) frequency at a point of maximum amplitude of spectral function in the high frequency band ($F_{HFmax}$);
ix) ratio of power of high frequency to power of low frequency 1, ($P_{HF}/P_{LF1}$);
x) ratio of power of high frequency to power of low frequency (sum of powers of low frequency 1 and low frequency 2), ($P_{HF}/(P_{LF1}+P_{LF2})$);
xi) heart rate (HR);
and, if a spectral peak falls in the range of a middle frequency band,
xii) ($S_{MF}$) maximum amplitude of spectral function in a middle frequency band; and
(b) applying a clusterization algorithm to the parameter values quantitated in step (a) so as to determine two further parameters, one of which correlates with sympathetic nervous system activity and the other of which correlates with parasympathetic nervous system activity.

In embodiments, the high frequency is 0.15 to 0.5 Hz; the low frequency 1 is 0.07 to 0.15 Hz; the low frequency 2 is 0.033 to 0.07 Hz.

In embodiments, parasympathetic nervous system activity is determined by the parameters: i) $P_{HF}$; ii) $P_{LF1}$; iii) $P_{LF2}$; and iv) $P_{LF1}$-$P_{HF}$.

In embodiments, the value of $P_{HF}$, $P_{LF1}$ or $P_{LF2}$ is one of 30 values.

In embodiments, each of the 30 values is an integer representing the sub-range of the power spectrum falling between each of the following numbers, in msec$^2$:

99999, 12000, 11000, 9000, 7800, 6400, 5200, 4200, 3200, 2500, 2100, 1700, 1300, 1000, 900, 820, 730, 640, 570, 490, 420, 360, 310, 255, 200, 145, 95, 55, 25, 15 and 0 for $P_{HF}$;

99999, 9000, 7800, 6400, 5200, 4200, 3400, 3000, 2600, 2200, 1850, 1550, 1300, 1100, 1000, 900, 810, 730, 640, 570, 490, 420, 350, 300, 250, 200, 150, 120, 70, 25 and 0 for $P_{LF1}$; and 99999, 9000, 7800, 6400, 5200, 4200, 3400, 3000, 2600, 2200, 1850, 1550, 1300, 1100, 1000, 900, 810, 730, 640, 570, 490, 420, 350, 300, 250, 200, 150, 120, 70, 25 and 0 for $P_{LF2}$.

In embodiments, sympathetic nervous system activity is determined by the parameters:
i) $P_{LF1}$;
ii) $P_{LF2}$;
iii) $S_{LFmax}$;
iv) $F_{LFmax}$;
v) $S_{HFmax}$;
vi) $F_{HFmax}$;
vii) $S_{MF}$ (if present);
viii) $P_{HF}/P_{LF1}$;
ix) $P_{HF}/(P_{LF1}+P_{LF2})$; and
x) HR.

In an embodiment, the method further comprises replacing an artifactual parameter value with an interpolated parameter value prior to step (c).

In an embodiment, in step (c) the frequency domain analysis comprises reducing the value of a power in a lower frequency subrange if the total power in the subrange of 0.5 to 1.0 Hz exceeds 3000 ms$^2$.

In an embodiment, prior to step (b) the data are subjected to a data preparation algorithm.

The method of claim 1, wherein in step (c) the frequency domain analysis is performed via a power spectral analysis algorithm.

In an embodiment a system is provided for characterizing autonomic nervous system activity of a patient comprising:
i) a processor; and
ii) a machine-readable medium tangibly embodying a program of instructions executable by the processor to perform the method.

In an embodiment the system comprises a display means to present results to a user thereof via a computer interface.

Experimental Details

Heart Rate Variability Analysis for ANS Assessment

It is well known that autonomic response is the first human response to any external intervention or to any physical, physiological, or psycho-emotional activity. Likewise, any pathological process will immediately provoke an ANS response. The main regulatory mechanism in heart rate variability (HRV) is autonomic regulation. Therefore, a HRV method is unique in its ability to assess the impact of any intervention or activity and to detect the early signs of pathological developments or functional disorders which may not be revealed by routine physical examination. HRV may be assessed via ECG recordings. References 5-11, incorporated by reference, relate to the interpretation of pathologies and physiological function from ECG data.

The present invention provides a method for quantitative assessment of sympathetic and parasympathetic activities on the basis of evaluating multiple parameters obtained by analysis of heart rate variability and representing them as two final values.

Spectral or other type of mathematical analysis of HRV generates multiple HRV parameters. The challenge of quantifying the relationship between sympathetic and parasympathetic branches is to derive from all the multiple parameters values just two values of the two target parameters: i.e. sympathetic activity level and parasympathetic activity level. The spectral analysis of HRV disclosed here produces 12 spectral components, resulting in 12 different values in a 12-dimensional coordinate system. The method, related to Minsky's Frame theory, transforms the 12-dimensional system into a 2-dimensional system, where the value of parasympathetic activity is on the horizontal axis and the value of sympathetic activity is on the vertical axis. Clustering the relationship between sympathetic and parasympathetic activities into up to 81 different states, creates a quantitative visualization of overall physiological status of the patient and assists physicians in patient assessment. In one embodiment, a system for implementation of the method is a software program installed on a personal computer that analyses R Wave interval signals collected by an ECG device, performs HRV analysis and quantitative ANS assessment, and displays results in a user-friendly interface.

To perform HRV analysis, an effective and transparent visual representation is used, known as the Method of Rhythmography which reflects HRV wave structure and serves as a "fingerprint" of autonomic regulatory mechanisms. The method was developed by D. Zheimaitite. ("The methodology for automatic analysis of rhythmograms and its clinical applications." PhD thesis, Kaunas, Lithuania, 1972.) This method, represented on FIG. 1, is based on representing the time intervals between consecutive heartbeats as straight vertical lines. The longer the interval between two heartbeats (RR), the longer the corresponding vertical line.

Figure 2:
FIG. 2 A rhythmographic strip composed of a stream of consecutive RR intervals.

When these lines are graphed sequentially, they form a Rhythmogram—a curve-specific wave portrait of RR intervals variability shown on FIG. 2. Rhythmographic representation allows a great deal of information to be compressed in a simple picture. The wave portrait in FIG. 2 is composed of 448 RR intervals of the ECG. A spectral analysis of this wave "portrait" allows an investigator to identify two main spectral components:

Low frequency: 0.033-0.15 Hz;
High frequency: 0.15-0.5 Hz.

Figure 3:
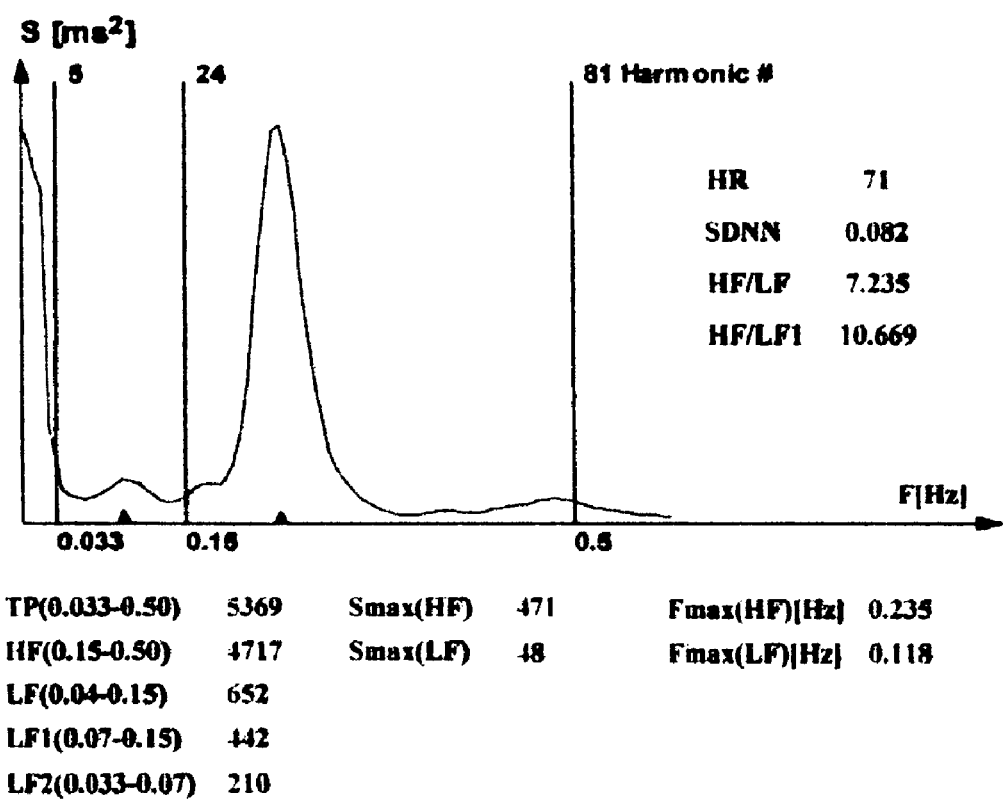
FIG. 3 Spectral chart with results of HRV analysis.

Spectral chart showing these parameters is displayed on FIG. 3.

A high degree of correlation has been established between the power of high-frequency band of the spectral function and the activity of Parasympathetic Nervous System (PSNS). A similar correlation has been demonstrated between the power of low-frequency band and the activity of Sympathetic Nervous System (SNS). These findings have been well documented in a number of medical and scientific publications and in conference reports ("Heart rate variability. Standards of measurement, physiologic interpretation, and clinical use. Task Force of the European Society of Cardiology and the North American Society of Pacing and Electrophysiology." *European Heart Journal*, 1996, 17: 354-381.)

Figure 4:
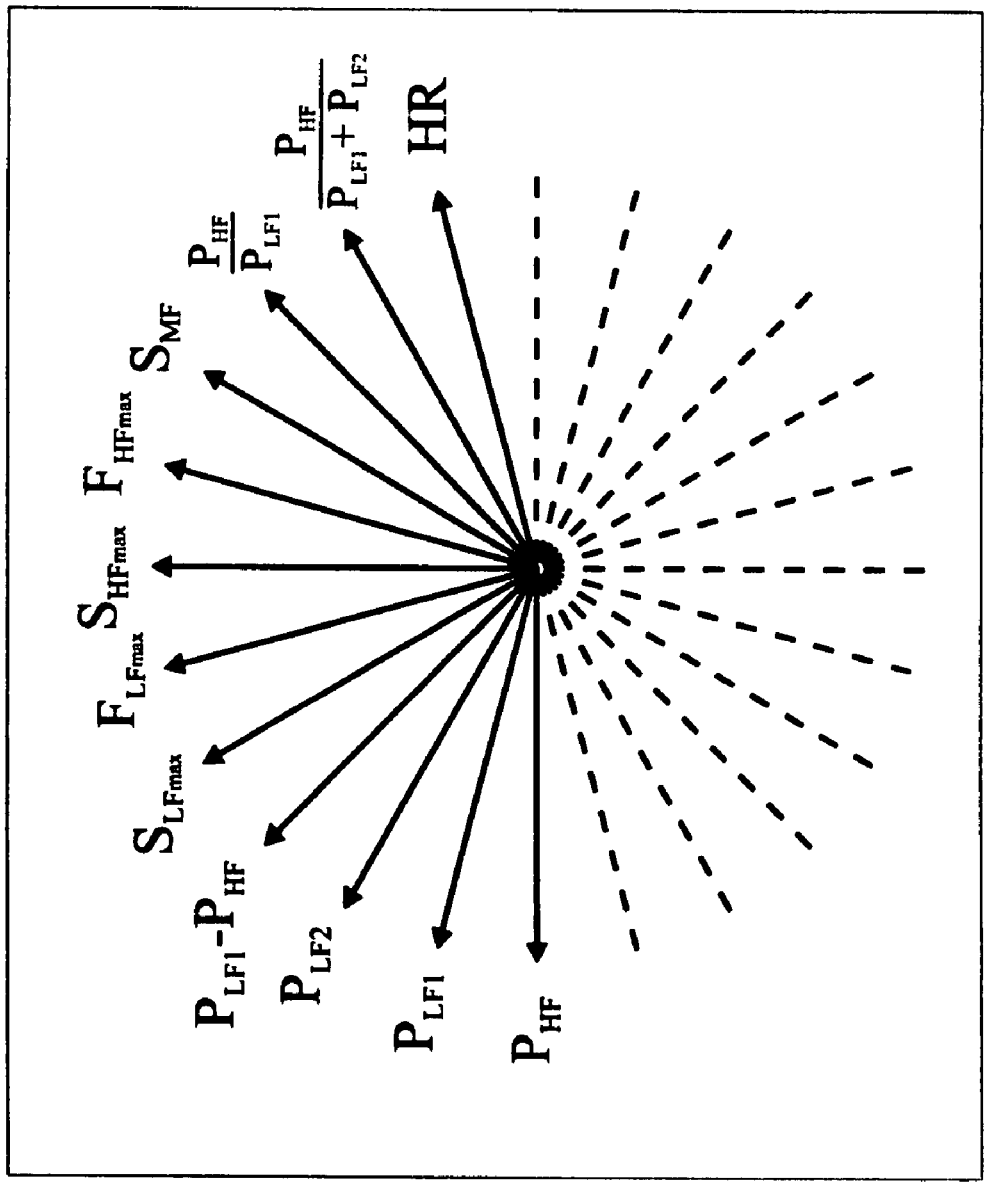
FIG. 4 Graphical representation of 12 spectral components in a 12-dimensional system of coordinates, each line ending with an arrow extends in a separate special dimension. The range of positive values is shown in solid lines while the range of negative values is shown as a dotted line; actual values of spectral parameters are only positive.

Spectral analysis generates multiple parameters of HRV. The challenge of SNS-PSNS quantification, is to reduce values of multiple parameters obtained from HRV analysis to only two final parameters: sympathetic activity level and parasympathetic activity level. The mathematical analysis of HRV disclosed herein produces 12 spectral components, resulting in 12 different values in a 12-dimensional coordinates system. This can be translated into a 2-dimensional system of coordinates as shown on FIG. 4 with the value of activity of PSNS on one axis and the value of activity of SNS on another axis. This final value quantitatively expresses the state of the autonomic nervous system of the tested individual. The description below pertains to clusterization of ANS states provided in an embodiment of the present method.

Clusterization of ANS States

The method provides cluster analysis of the ANS states: it recognizes different types of relationship between SNS and PSNS activities and assigns these types into clusters. It identifies up to 81 ANS states, and groups them into 9 categories of ANS conditions.

Figure 5:
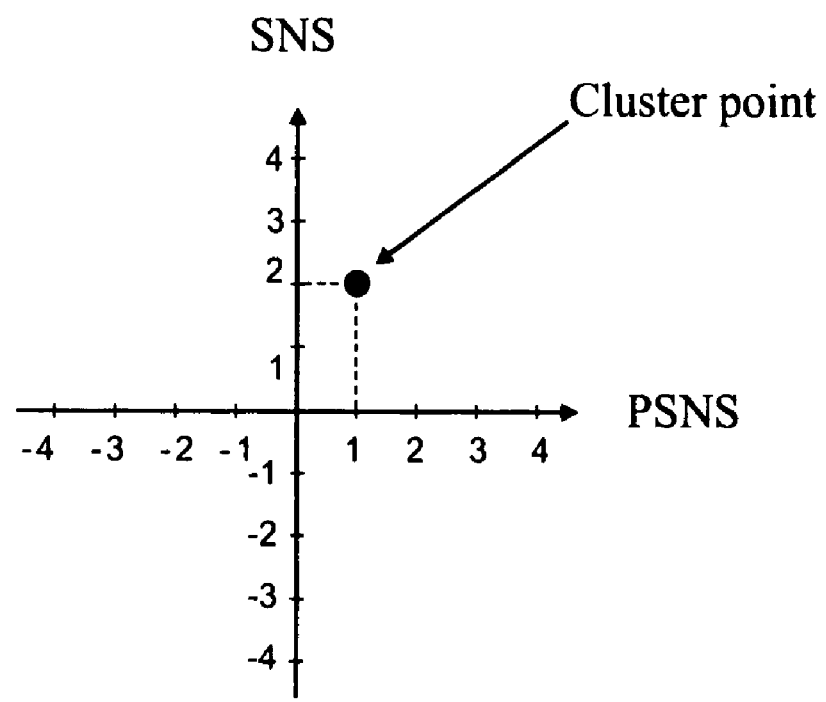
FIG. 5 PSNS and SNS parameters in a 2-dimensional system of coordinates. The displayed point reflects the relationship between activities of PSNS and SNS, PSNS value of the point being the x-coordinate while SNS value being the y-coordinate.
Figure 6:
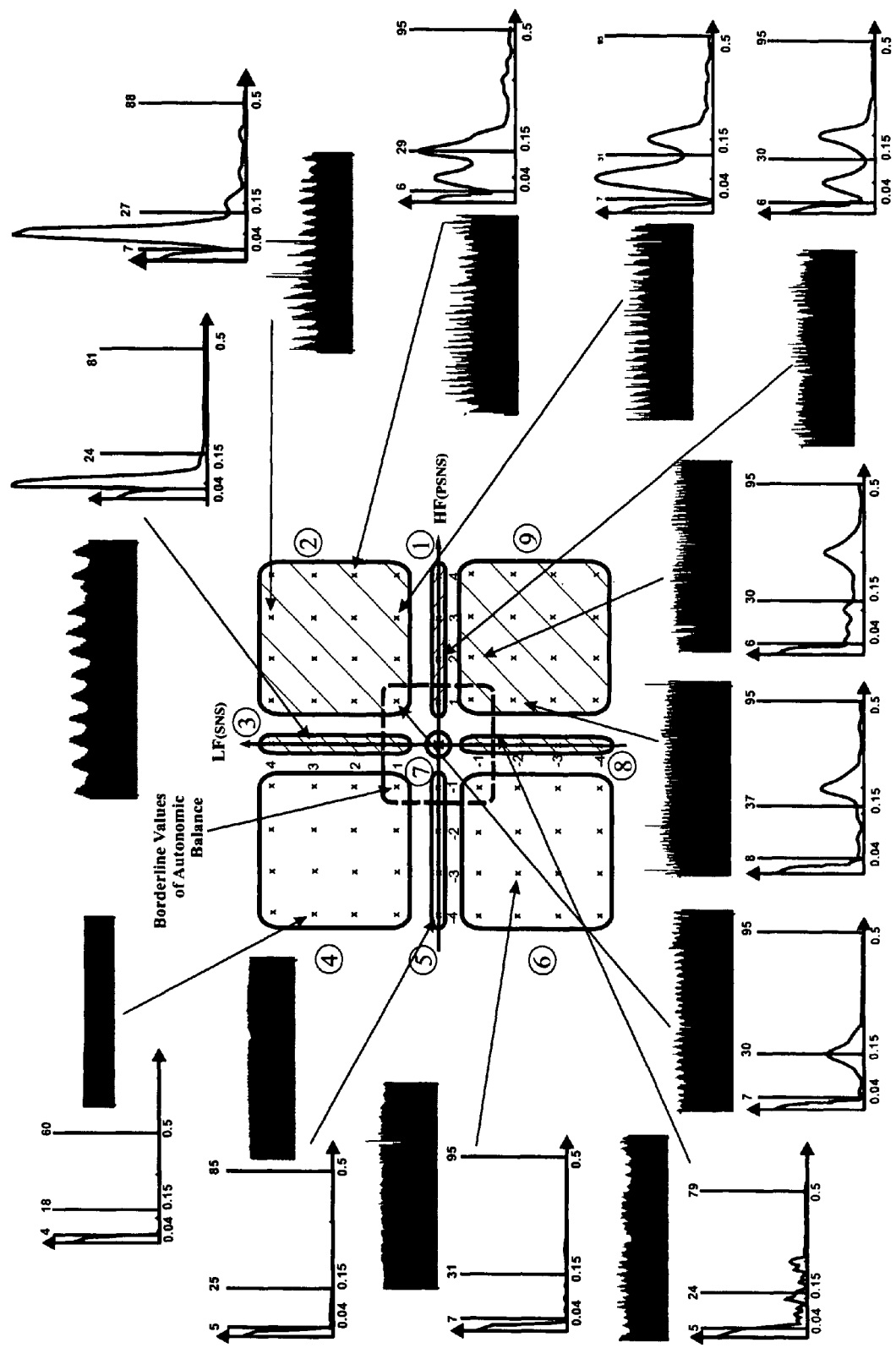
FIG. 6 Diagram of the clusterization of the autonomic nervous system's states provided by the present method illustrating how, based on HRV analysis, the method quantifies the relationship between SNS and PSNS into 9 categories and up to 81 different types with examples of corresponding spectral charts and rhythmograms.

The method then graphs the parasympathetic activity on the horizontal, or X-axis and the sympathetic activity on the vertical, or Y-axis (FIG. 5 and FIG. 6). The intersection point of the sympathetic and parasympathetic axes is the point of autonomic balance. To the right of and above this balance point, the method displays an area of increased parasympathetic and sympathetic activities in 4 gradations. Decreases in PSNS and SNS activities are shown to the left and below the balance point.

81 ANS states are subdivided into nine categories (circled in FIG. 6, with corresponding numbers marking each category—e.g., 1, 2):

Category 1 PSNS prevalence with average level of SNS activity is illustrated by 4 points:
  Point 1 represents a slight PSNS prevalence;
  Point 2 represents a moderate PSNS prevalence;
  Point 3 represents a significant PSNS prevalence;
  Point 4 represents a sharp PSNS prevalence;
Category 2 A simultaneous increase in both PSNS and SNS activities, with different variations, is illustrated by 16 points;
Category 3 SNS prevalence is illustrated by 4 points (slight, moderate, significant, and sharp);
Category 4 PSNS decrease with an SNS increase is illustrated by 16 points;
Category 5 PSNS decrease with the average level of SNS activity is illustrated by 4 points (slight, moderate, significant, and sharp);
Category 6 A general decrease in both SNS and PSNS activities is illustrated by 16 points;
Category 7 A point at zero value on the coordinate system indicates ANS balance;
Category 8 SNS decrease with average level of PSNS is illustrated by 4 points (slight, moderate, significant, and sharp);
Category 9 Increase in PSNS with a decrease in SNS is illustrated by 9 points.

Test Modalities for Monitoring ANS Reaction

Different test modalities have been widely established for monitoring reaction of the ANS to specific stimuli:
 1. Lying-to-standing, or the orthostatic test as the initial method for ANS provocation;
 2. Valsalva maneuver combined with deep breathing as the optimal method for revealing the hidden abilities of the autonomic function and distinguishing between chronic and temporary abnormalities;
 3. Real-time monitor test as the ultimate method for ANS assessment in long-term therapy, continuous monitoring (especially, under anesthesia/intensive care), research and experimentation.

A proper evaluation requires measurements of a patient under at least two different conditions. The method here is used to examine a patient both at rest and during physical activity. This can be accomplished by having a patient engage in some activity where the general response of a healthy person is known. Based on the patient's reaction, a more accurate assessment of ANS is possible.

Orthotest as a Method of ANS Assessment

The method uses the orthostatic test, or lying-to-standing test, as a popular means of ANS provocation, when the patient moves from a supine to a standing position. Any physical or mental dysfunction can be exhibited as an inadequate ANS response during this test.

Figure 7:
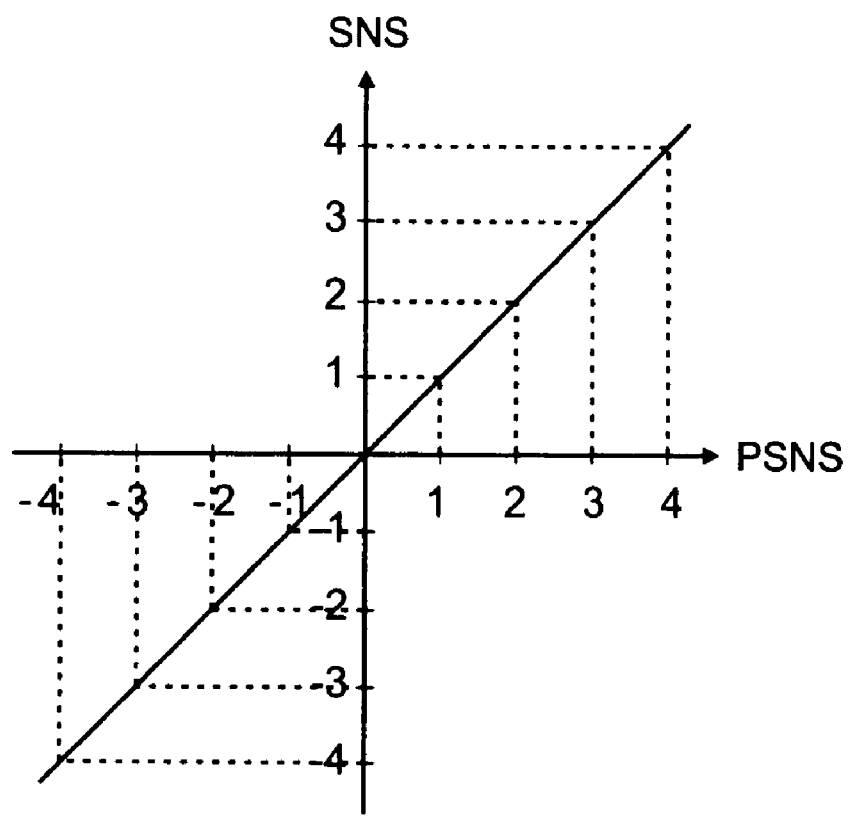
FIG. 7 Graph showing points along a bisecting line with equal values of SNS and PSNS activity.

NOTE. The most important group of points among the 74 recognizable possibilities is the group along the line bisecting the [0,0] coordinates as shown in FIG. 7. This line contains 9 points (including [0,0]) with numerically equal coordinates. Formally, these points may be considered points of autonomic balance due to their characteristic parity of PSNS and SNS activity. Thus the point [0,0] may be interpreted as a point of balance in the general activity of PSNS and SNS which correlates with the accepted notion of "vegetative homeostasis". It is important to realize that a slight increase [1, 1] or a slight decrease [−1.−1] still reflects a normal average level of the traditional notion of "vegetative homeostasis", but any deviation outside of these parameters, though mathematically still balanced, must not be interpreted as a clinical homeostasis. Children, however, will typically show a moderately to sharply increased balance.

Figure 8:
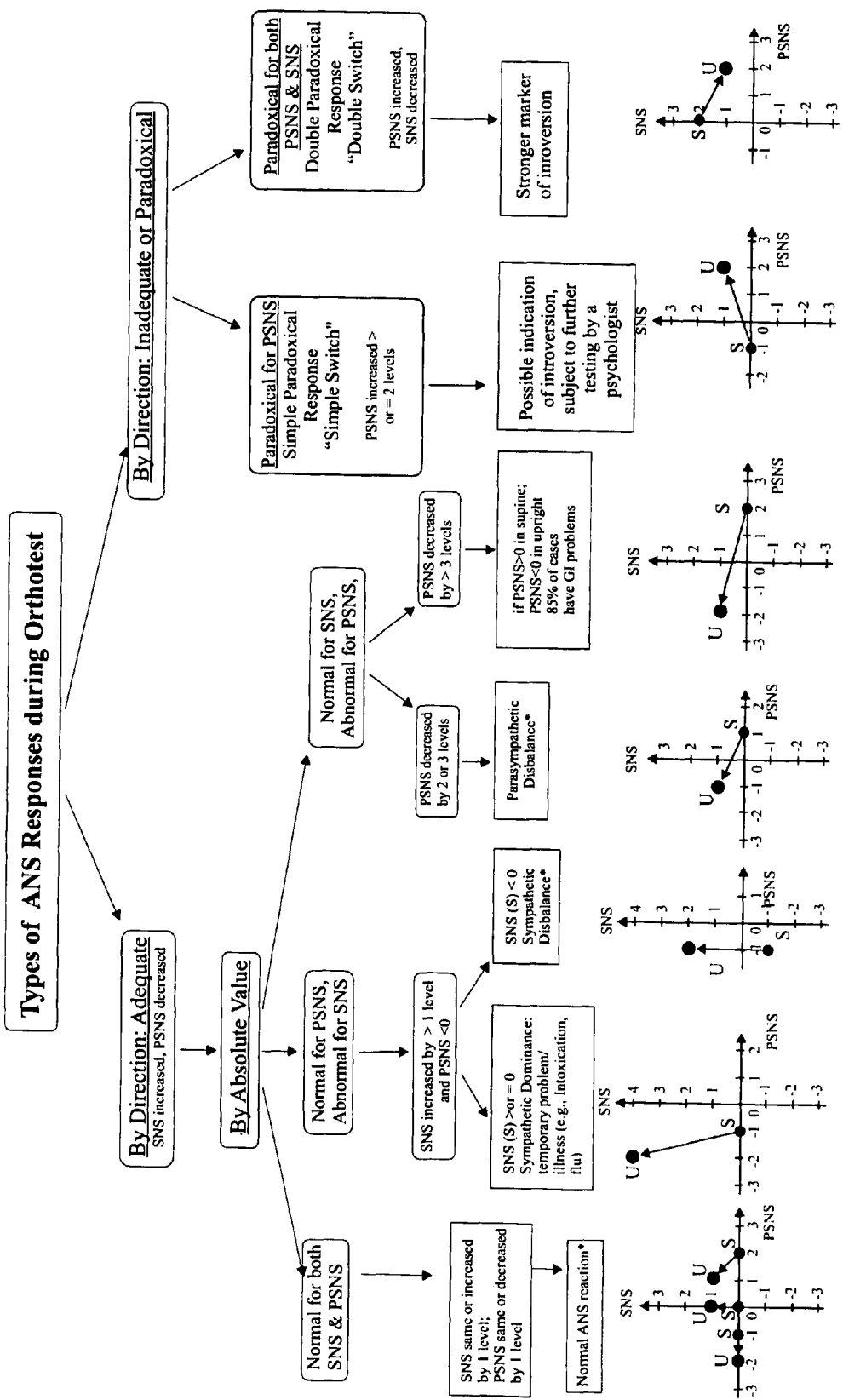
FIG. 8 Flow chart for types of autonomic nervous system (ANS) responses during an orthostatic test including illustrations and physiological interpretations (diagnosis)

Common types of reaction to orthostatic intervention are shown in FIG. 8 with illustration and possible physiological interpretations.

The orthostatic test (orthotest) and Valsalva maneuver combined with deep breathing test together form an overall picture of the patient's physiological functioning. While the orthotest reflects current status of the organism, the Valsalva test shows functional reserves of the ANS.

Valsalva Maneuver Combined with Deep Breathing as a Method of ANS Assessment

NOTE: Valsalva maneuver combined with deep breathing is further referred for convenience as "the Valsalva test."

The test provides two types of results:
1. Valsalva index;
2. Comparative analysis of the ANS status of normal vs deep breathing (reflected on the ANS chart).

The latter result is by far more reliable and informative. The test "Valsalva maneuver combined with deep breathing" is targeted to reveal changes from normal to deep breathing and to compare these two stages. The Valsalva maneuver itself is auxiliary in this test and is used as a stimulus to induce these changes by activating baroreceptors and receptors of the ANS.

Interpretation of Valsalva Index

The calculated Valsalva index falls into one of the three zones:
>1.7-High level;
1.3-1.7-Average level; and
<1.3-Low level.

Based on prior research, it has been established that the transitional process in the Valsalva is practically impossible to standardize since Valsalva the maneuver is an act of will and, therefore, is determined by many subjective factors due to variations in individual physiology and psycho-emotional makeup (e.g. persons with special training such as Air Force or Navy personnel are more adaptable to the Valsalva maneuver). A classical transition process during the Valsalva, which serves as a basis for calculating the Valsalva index, does exist, but in real life it is observed in only a small percent (about 10-15%) of population. Thus, while a good Valsalva index is significant, a poor Valsalva index may have no clinical significance: it may merely result from a poor control by the patient or a lack of training. In case of a low Valsalva index, the test results should be interpreted in terms of comparison of HRV response during normal and deep breathing.

Interpretation of ANS chart (clusterization chart of HF (PSNS) versus LF (SNS) components) in the Valsalva test:

The Valsalva maneuver combined with deep breathing test is targeted to assess functional reserves of both sympathetic and parasympathetic branches of the ANS.

In interpreting the results of this test on the clusterization chart, both the position of the points and the dynamics of the test should be taken into the consideration. The types of ANS responses to Valsalva test are described below.

One way to interpret a patient's test results is to first analyze the reaction of the parasympathetic nervous system (PSNS), then the reaction of the sympathetic nervous system (SNS), and, finally, to superimpose the two results in order to create an overall picture of ANS reaction.

Assessment of response of Parasympathetic Nervous System (PSNS) during the Valsalva test:

For separate analysis of response of the PSNS, the trends are considered when SNS remains unchanged while the PSNS system response varies. GENERAL TREND: Independently on the position and dynamics of SNS, an increase in PSNS activity from normal breathing to end of test usually indicates that functional reserves of the PSNS come into action; the larger the increase, the greater the reserves of the PSNS.

Figure 9:
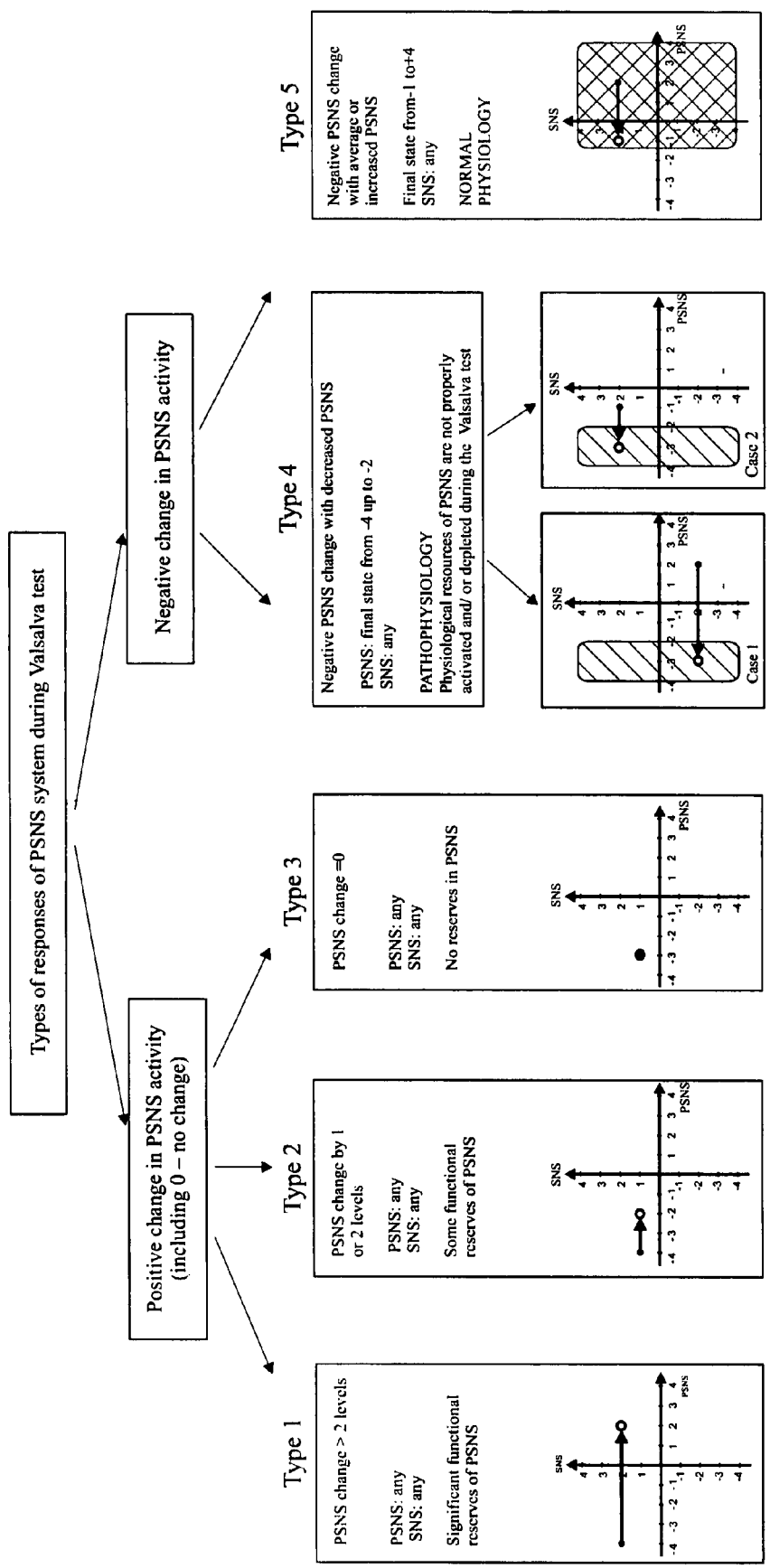
FIG. 9 Flow chart for types of PSNS responses during Valsalva test including illustrations and physiological interpretations.

Different types of responses of PSNS are shown in FIG. 9. Each type has a range of values that fall into that type, and a specific example is given below to represent one of all possible cases of this type. The range of values for the final position of PSNS is shown by shaded area of the graph.

Figure 10:
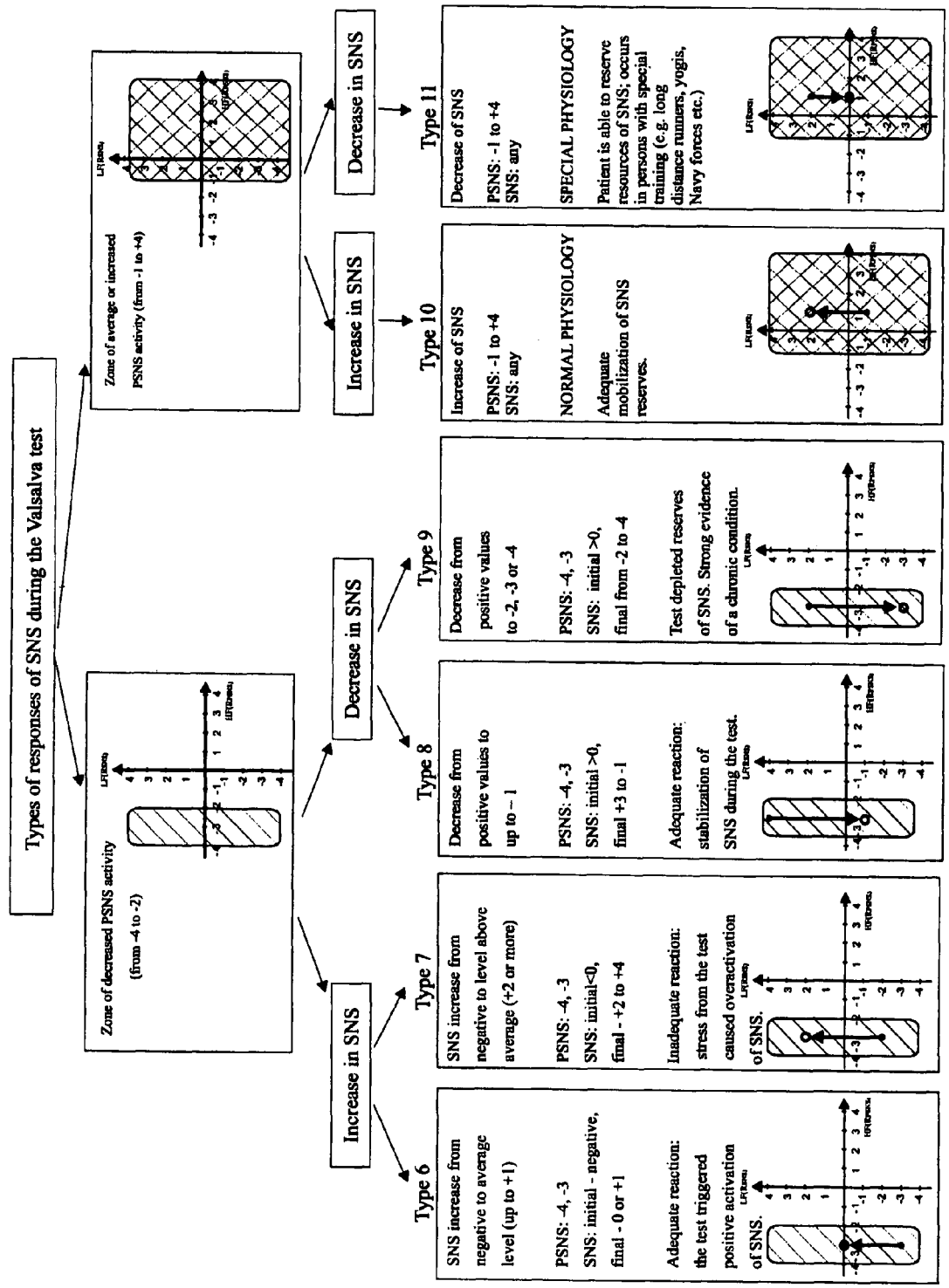
FIG. 10 Flow chart for types of SNS responses during Valsalva test including illustrations and physiological interpretations.

Assessment of response of Sympathetic Nervous System (SNS) during Valsalva test Reaction of SNS can be evaluated depending on the position of PSNS: the two zones where the PSNS reaction can fall into are shown in FIG. 10 in the shaded area.

The −1 Position of PSNS activity can be considered a borderline value. If the initial position of SNS is 0, any SNS decrease indicates stabilization of the sympathetic branch. If SNS from positive values decreases to 0, this characterizes a borderline condition and can indicate either a normal or an inadequate reaction depending on other manifestations of the patient's clinical condition.

Figure 11:
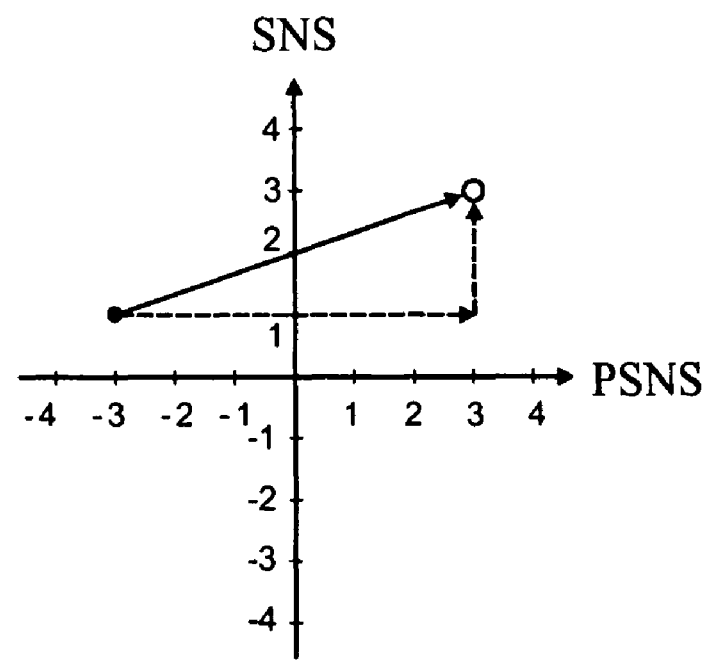
FIG. 11 Graphical Interpretation of a mixed response when both SNS and PSNS change during Valsalva test.

Interpretation of mixed responses when both SNS and PSNS change:

In most cases, the test demonstrates a mixed response when both SNS and PSNS change after performing the Valsalva maneuver and deep breathing. To interpret the result, the arrow representing the ANS response can be treated as a vector and can be broken down into the vertical (SNS) and horizontal (PSNS) components as shown below in FIG. 11. The example in FIG. 11 can be interpreted in the following way:

PSNS, or horizontal component, changes from −3 to +1, which corresponds to significant functional reserves of PSNS; and SNS, or vertical component, falls into zone #2 according to FIG. 10 (positive PSNS). Increase of SNS activity corresponds to normal physiologic response, indicating adequate mobilization of SNS reserves.

Real-Time ANS Monitoring

The proposed method enables ANS assessment in "real-time" mode, which means that data is analyzed as it is put it. Results can be produced and updated with certain periodicity (the physician can choose the results update frequency, or refresh rate).

In spite of some simplicity of the "real-time" mode, it is essentially universal since it enables the autonomic response assessment during different kinds of long-term therapy, controlled exercises or during any kind of experiments aiming at therapeutic strategy optimization.

Figure 12:
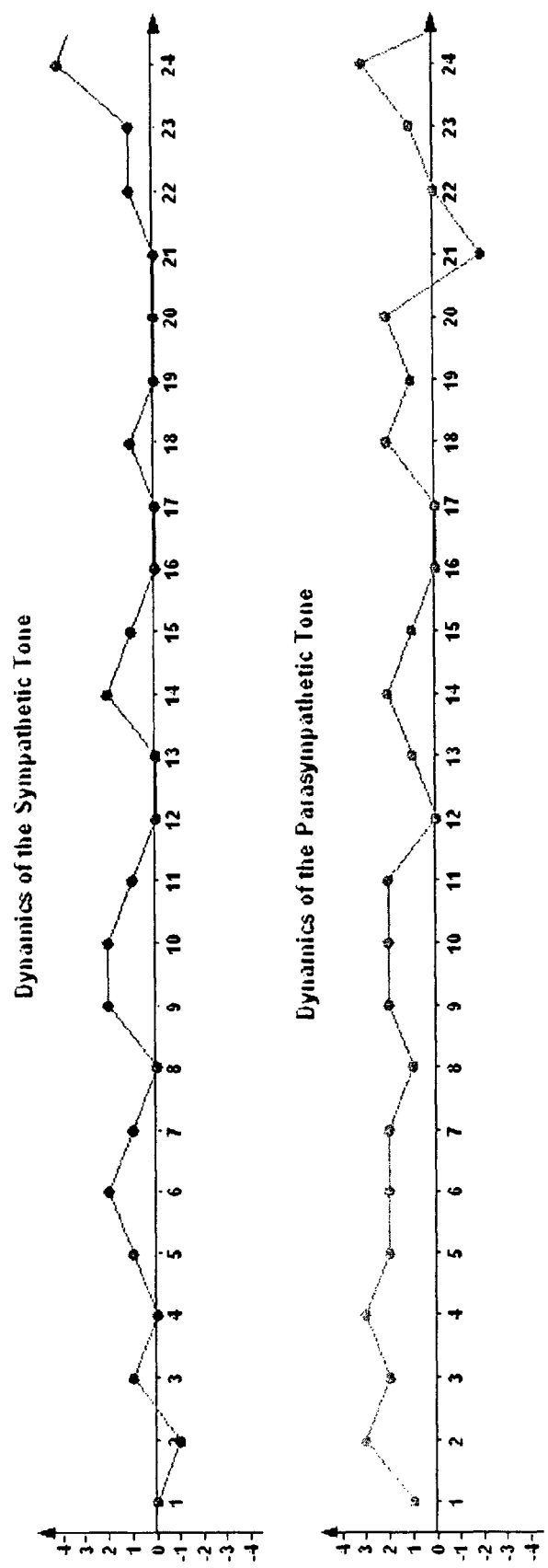
FIG. 12 Illustration of the dynamics of PSNS and SNS during Real-time ANS assessment provided by the method.

The ANS chart in this type of test modality can be represented as shown in FIG. 12. In this graphical representation, dynamics of SNS and dynamics of PSNS are displayed on separate two-dimensional charts, where the test progress is displayed on the X-axis while the reaction of the corresponding branch of the ANS is displayed on the Y-axis.

Figure 13:
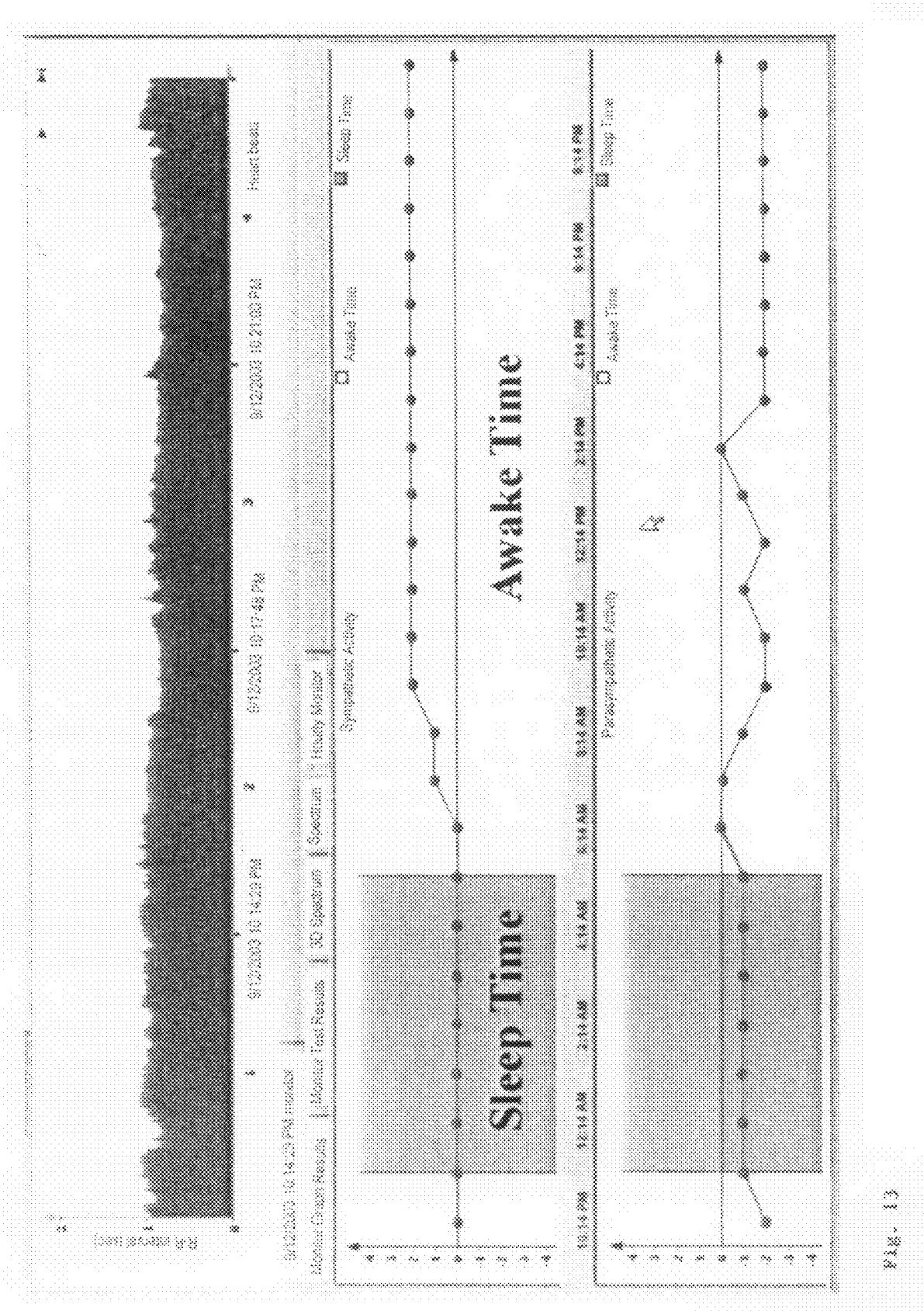
FIG. 13 Illustration of hourly monitor as a feature of HRV assessment.

Hourly Monitor as a Feature of Real-Time Assessment:

With this feature, ANS activity can be monitored continuously and the dynamics of autonomic function during up to 24 hours can be shown at once as displayed on FIG. 13. The hourly monitor allows comparison of ANS activity during daytime and night-time, which is the key to detecting health abnormalities of two kinds:
1. Detecting serious health impairments: seeing the difference between daytime and nighttime activity of the ANS system is critical for distinguishing between a temporary health problem and a serious disorder.
2. Detecting sleep disorders: instability of parasympathetic nervous system activity during sleep beyond the normal range is a marker of a sleep disorder.

FIG. 12 shows dynamics of SNS and PSNS during sleep time and wake time.

Algorithm Description

In an embodiment the method for ANS assessment comprises the following steps:
1. Data preparation for spectral analysis of HRV;
2. Spectral analysis which generates values of 12 HRV parameters; and
3. Clusterization of the results obtained from step 2: transformation of values of 12 parameters into values of 2 parameters: activity of PSNS and activity of SNS.

The algorithm includes the following three corresponding stages of data treatment, which are described in more detail below:
1. Algorithm for data preparation for spectral analysis, including treatment of artifacts and ectopic beats in the data stream;
2. Algorithm for spectral analysis of HRV including automatic correction of power spectrum results in the presence of artifacts and ectopic beats; and
3. Algorithm for clusterization into up to 81 ANS states based on relationship between PSNS activity and SNS activity.

Algorithm for Data Preparation for Spectral Analysis

Many prior systems use ECG data as source data while the disclosed method uses RR intervals. Any source data of heart signals from patient usually includes interference signals, or artifacts, and ectopic beats, also referred to as extrasystoles, which are present in source data. If not appropriately treated, artifacts and ectopic beats can significantly affect HRV measurement, hence any system for HRV analysis faces the challenge of recognition and removal or other kind of treatment of artifacts and ectopic beats. Other methods, which usually work with ECG data, predominantly use morphological analysis of ECG for removal. However, working with RR interval stream, using direct automated analysis of data, which includes automated removal of artifacts and ectopic beats, confers advantages. Since this method skips the intermediate step of morphological analysis of ECG, it reduces the time and cost of HRV analysis.

Specific routines disclosed herein process interference and extrasystoles (ectopic beats) in the RR data stream, which are based on the method proposed by Chireikin, L. V. Shurygin D. Ya., and Labutin V. K. (L. Chireikin, D. Shurygin, and V. Labutin, Automatic Analysis of Electrocardiograms (Russian), Nauka, Leningrad, 1977).

To increase precision of the HRV assessment in the presence of artifacts, this can be combined with an additional new method implemented on the stage of power spectral analysis, described hereinbelow.

On the stage of data preparation, the algorithm uses specific operations that differentiate between types of artifacts and ectopic beats. For internal operation of the algorithm, different labels were assigned to different types of ectopic beats. Hereinafter, differentiation between ectopic beat types and patterns (such as ventricular extrasystoles ($ES_v$), supraventricular extrasystoles ($ES_{SV}$), dropped QRS complex ($QRS_{dr}$), bigeminy, trigeminy and quadrigeminy) has only internal meaning for mathematical treatment of data within the algorithm and has no clinical significance. Since morphological analysis of ECG is not used, only consecutive RR intervals, one cannot determine the types of encountered ectopic beats. Hence, the terms mentioned above serve as mnemonic labels in operation of the algorithm that help to differentiate between types of ectopic beats and wave patterns.

In automated data preparation extrasystoles can be recognized only indirectly based on average statistical assessment of the duration of the compensatory pause, the duration of the pre-ectopic beat interval and some additional procedures. The recognized extrasystoles and interference are replaced with interpolated values. During interpolation it is necessary to preserve the wave structure of RR intervals sequence in such a way that it does not affect calculation of parameters of spectral function, mainly high frequency and low frequency.

The analyses are performed in the following sequence:
1. Recognition of artifacts and ectopic beats and their interpolation (replacement with interpolated values).
2. Recognition of patterns of ectopic beats such as bigeminy, trigeminy and quadrigeminy. For each of these patterns the conclusion is based on several factors: the calculated number of extrasystoles, the way they are combined, and the sequence of their recognition.
3. Recognition of ectopic beats such as isolated ventricular extrasystoles ($ES_v$), also called premature ventricular contractions (PVC), supraventricular extrasystoles ($ES_{SV}$), interpolated ventricular extrasystoles ($ES_{vi}$) and dropped QRS complexes ($QRS_{dr}$) by a strict algorithm based on analyzing 5-6 pairs of adjacent R-R intervals.
4. Generation of a histogram of ectopic beat intervals for estimated placement of extrasystoles.
5. Analysis of results of the recognition of ectopic beat and artifact patterns, isolated extrasystoles and dropped QRS complexes ($QRS_{dr}$) for making the internal conclusion about the presence and type of extrasystoles. In this approach error can occur only in determining the amount of recognized extrasystoles and in case of multiple extrasystoles, when the precise recognition of the number of ectopic beats and artifacts is not critical.

In order to perform the analysis, first it is necessary to recognize specific combinations of adjacent pairs of intervals characteristic of each type of extrasystoles and to compute their number.

Figure 14:
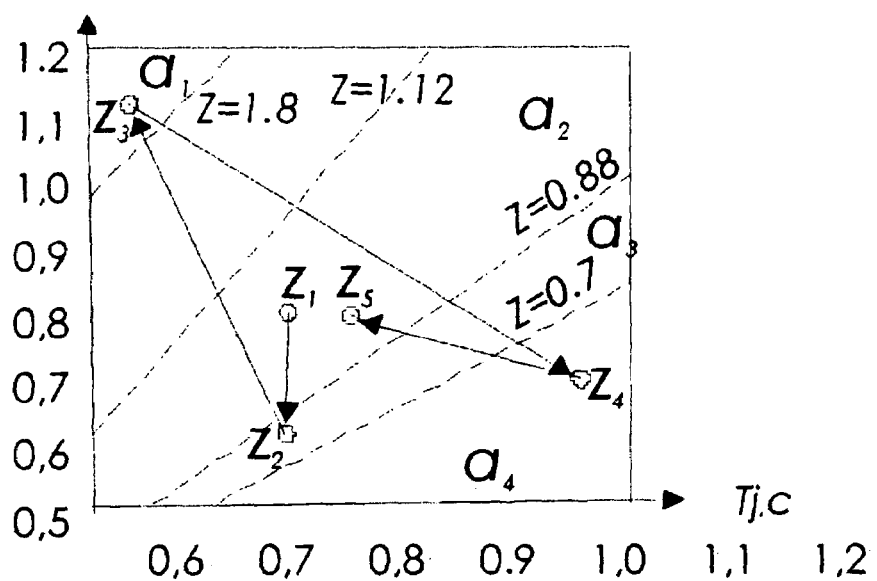
FIG. 14 An isolated ventricular extrasystole ($ES_v$) pattern on the plane $T_j$, $T_{j+1}$ during recognition of artifacts ($ES_v$ and $ES_A$) which is used in the present method.

For this analysis, a method of scatterography is used, illustrated in FIG. 14. In this method a plane is formed by the axis $T_j$ and $T_{j+1}$, where the values of the length of the interval $X_i$ are added on the $T_j$ axis and the length of $X_{i+1}$ is the value on the $T_{j+1}$ axis. Every pair of adjacent intervals is thus represented as a point $Z_i$ on the plane, and every sequence of intervals is the set of points $\{Z_1, Z_2, \ldots, Z_{n-1}\}$. Analysis of the sequence of $Z_i$ values for recognition of ectopic beat patterns, isolated extrasystoles and $QRS_{dr}$ at rest and during controlled exercise such as Orthotest, as well as recognition of isolated interference signals allows to distinguish specific patterns of sequences of $Z_i$ values on the $T_j$ and $T_{j+1}$ plane.

Figure 15:
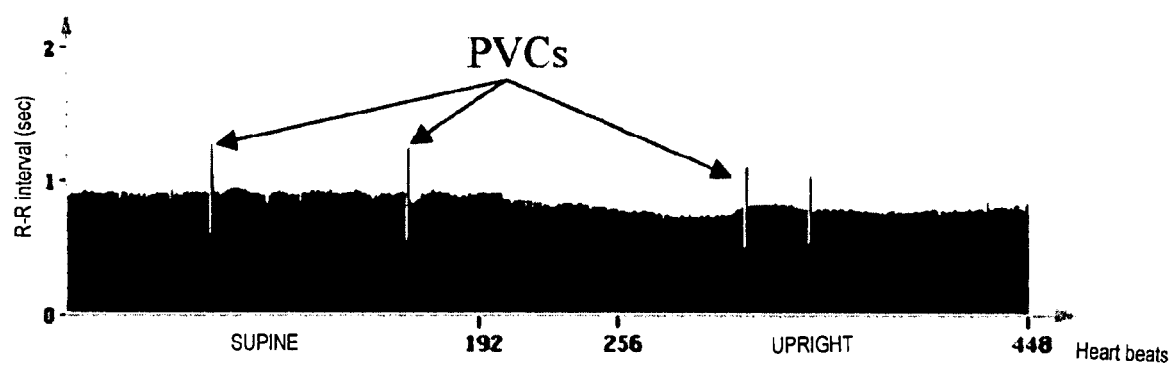
FIG. 15 Example of a rhythmographic strip with detected isolated ESv.

FIG. 14 shows the $ES_v$ pattern on the plane $T_j$, $T_{j+1}$, while FIG. 15 is the rhythmographic strip with detected isolated $ES_v$.

For example, during the isolated ventricular extrasystoles ($ES_v$), one can notice a pattern of $Z_i$ sequence, which can be represented as a logical vector $Z_{ESv}$ which has the value of 1 if all of its conditions are met, and has the value of 0 if at least one condition is not satisfied.

$$Z_{ESv} = \{(Z_1 \in A_2)\char`\^(Z_2 \in A_3)\char`\^(Z_3 \in A_1)\char`\^(Z_4 \in A_4)\char`\^(Z_5 \in A_2)\}.$$

Figure 16:
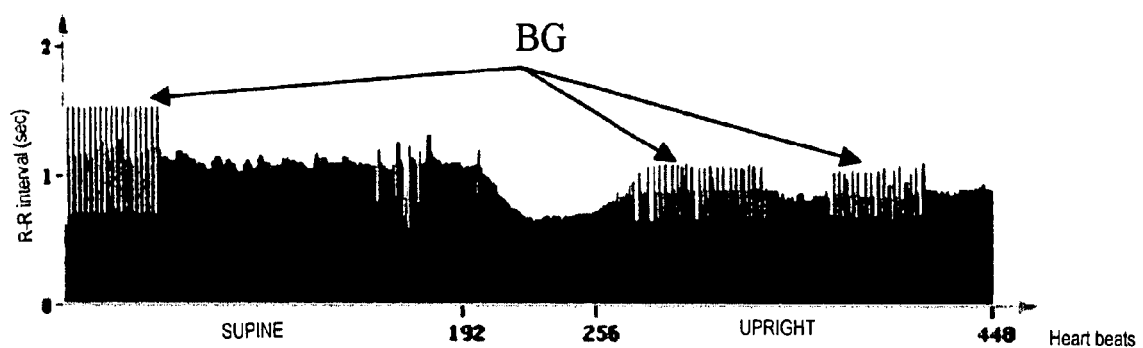
FIG. 16 Rhythmographic strip with artifacts like bigeminy in the supine and upright positions during orthostatic test.
Figure 17:
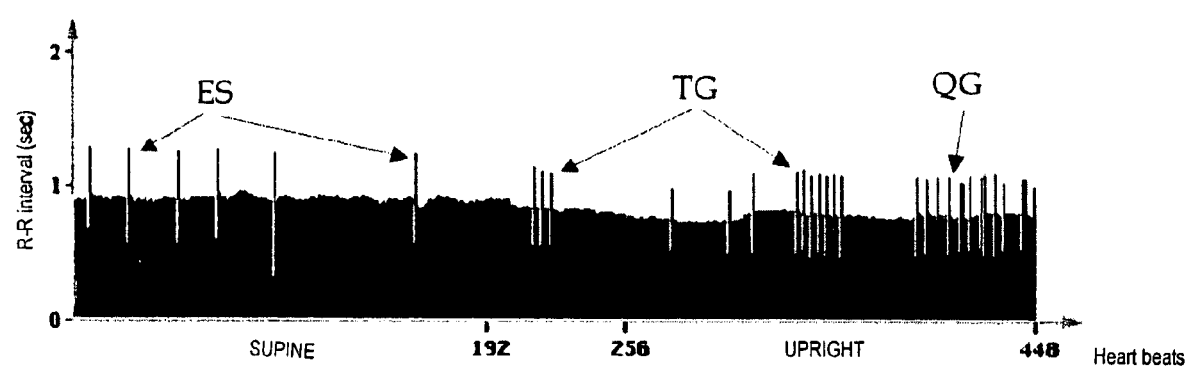
FIG. 17 Rhythmographic strip with isolated artifacts ($ES_i$), and trigeminy (TG) and quadrigeminy (QG) artifacts.

Recognition of patterns of artifacts and ectopic beats occurs in cycles. The dynamics of $Z_i$ values in each cycle of recognition of ectopic beat patterns is described by the vector Z. The number of cycles of recognition occurred without sequence interruption reflects the length and the nature of the complex. FIG. 16 is an example of a rhythmographic strip with registered bigeminy (BG); FIG. 17 shows rhythmographs with registered isolated extrasystoles ($ES_i$), trigeminy (TG) and quadrigeminy (QG).

Figure 18:
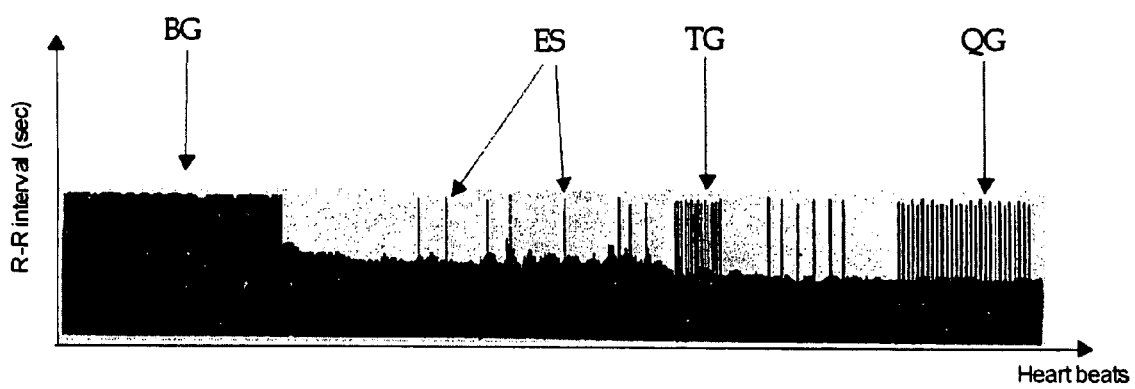
FIG. 18 Illustrates of bigeminy, isolated ESv, trigeminy and quadrigeminy with undetected QRS complexes artifacts.

There is a way to recognize patterns with undetected (deformed) QRS complexes. Automatic recognition of bigeminy in this case is extremely challenging, since concealed bigeminy (in case of undetected QRS complexes) and acute bradycardia is practically undistinguishable. Recognition in this situation is possible during exercise loads, when the RR interval is almost two times shorter; during exercise bigeminy appears as trigeminy, quadrigeminy and isolated extrasystoles. Therefore, trigeminy is recognized as bigeminy (with detected QRS complexes), and quadrigeminy as trigeminy (with detected QRS complexes). Isolated $QRS_{dr}$ will signal the presence of undetected QRS complexes, which is taken into account by the algorithm of recognition. FIG. 18 shows ectopic beats like bigeminy, isolated ESv, trigeminy and quadrigeminy with undetected QRS complexes. This will allow correct recognition of $ES_v$ (PVC).

Algorithm of artifacts and ectopic beats recognition and their qualitative evaluation can be represented as a 3-step sequence.

1. Consecutive determination of logical values of vectors $Z_{TG}$, $Z_{BG}$, $Z_{ESv}$, $Z_{ESi}$, $Z_{QRSdr}$, $Z_{TG(undetectedQRS)}$, $Z_{QG(undetectedQRS)}$, $Z_{interference}$ on analyzed value sequence Zi, where i=(1, . . . , N−1).
2. Calculation of the number of recognized isolated extrasystoles and cycles of recognition of ectopic beat patterns.
3. Replacement of recognized $RR_{ES}$, $RR_{CP}$ (CP—compensatory pause) and $RR_{interference}$ with interpolated values.

Every vector is assigned a number j:

j=1 for $Z_{ESv}$; j=2 for $Z_{ESsv}$; j=3 for $Z_{iterpol.}$; j=4 for $Z_{BG}$; j=5 for $Z_{TG}$; j=6 for $Z_{QG}$; j=7 for $Z_{TG\text{-}undetectedQRS}$; j=8 for $Z_{QG\text{-}undetectedQRS.}$; j=9 for $Z_{QRSdr.}$; j=10 for $Z_{interference}$. For each vector $Z_j$ the program registers the number of recognitions of this vector—$K_j$. Besides, for registering the amount of recognition cycles performed without interruption of $Z_i$ sequence, the variable $L_r$ is used (cycles count) where r ranges from 4 to 8 is the number of the vector $Z_j$, for which the number of cycles is being calculated by the algorithm.

Algorithm for Power Spectral Analysis and for Correction of Power Spectral Results in the Presence of Artifacts The system uses frequency domain approach as a method of characterizing fluctuations of RR intervals. We chose Fast Fourier Transform to implement the frequency domain approach.

Introduction to Fast Fourier Transform:

It is well known that any periodic discrete function f(x) may be presented as Fourier series with constants $a_p$, p=0, 1, . . . , 2N, $b_p$, p=1, 2, . . . , 2N, $$f_n = a_0/2 + \sum_{p=1}^{N}\left(\begin{array}{l}a_p\text{Cos}(2\pi np/(2N+1))+\\ b_p\text{Sin}(2\pi np/(2N+1))\end{array}\right), \quad (1)$$

$$n = 0, 1, \ldots, 2N$$

where $f_n$ are values of function f(x) at the points $$x_n=2\pi n/(2N+1), n=0, 1, \ldots, 2N. \quad (2)$$

Solution of the system (1) is well known [1]:

$$a_p = 2/(2N+1)\sum_{n=0}^{2N} f_n\text{Cos}(2\pi np/(2N+1)), \quad (3)$$

$$b_p = 2/(2N+1)\sum_{n=1}^{2N} f_n\text{Sin}(2\pi np/(2N+1)). \quad (4)$$

Power Spectral Density is calculated as $a_p^2+b_p^2$.

The discrete Fourier transform algorithm (DFT) calculates the values of coefficients $a_p$, $b_p$. The fast Fourier transform (FFT) [1] is a DFT which reduces the number of computations needed for N points from $2N^2$ to $2N \log_2 N$, where $\log_2 N$ is the base-2 logarithm.

Algorithm of Fast Fourier Transform:

This section describes the algorithm of the efficient calculation of $a_p$, $b_p$ from (3) and (4). It can be accomplished with only two trigonometric functions look-ups, namely for the numbers $\text{Cos}(2\pi/(2N+1))$ and $\text{Sin}(2\pi/(2N+1))$.

For each p=0, 1, . . . , N the numbers $U_{np}$ defined recursively by $$U_{2n+2,p}=U_{2n+1,p}=0, \quad (5)$$

$$U_{np}=f_n+2(\text{Cos}(2\pi p/(2N+1)))U_{n+1,p}-U_{n+2,p}, n=2N, 2N-1, \ldots, 1. \quad (6)$$

Then, following [1], $$a_p=2/(2N+1)(f_0+U_{1p}\text{Cos}(2\pi p/(2N+1))-U_{2p}), \quad (7)$$

$$b_p=2/(2N+1)U_{1p}\text{Sin}(2\pi p/(2N+1)). \quad (8)$$

Calculation procedure in Fast Fourier Transform:
Let $C_p=\text{Cos}(2\pi p/(2N+1))$, $S_p=\text{Sin}(2\pi p/(2N+1))$.
Input quantities are N, $C_1$, $C_2$, $f_n$ for n=0, 1, . . . , 2N.
1) To start, set $C_0=1$, $S_0=0$.
2) Then calculate for each p $$U_{2N+2}=U_{2N+1}=0,$$

$$U_n=f_n+2C_pU_{n+1}-U_{n+2}, n=1, 2, \ldots, 2N.$$

$$a_p=2/(2N+1)(f_0+C_pU_1-U_2),$$

$$b_p=2/(2N+1)S_pU_1.$$

3) If p=N, Stop.
If p<N, calculate $$C_{p+1}=C_1C_p-S_1S_p,$$

$$S_{p+1}=C_1S_p+S_1C_p.$$

Figure 19:
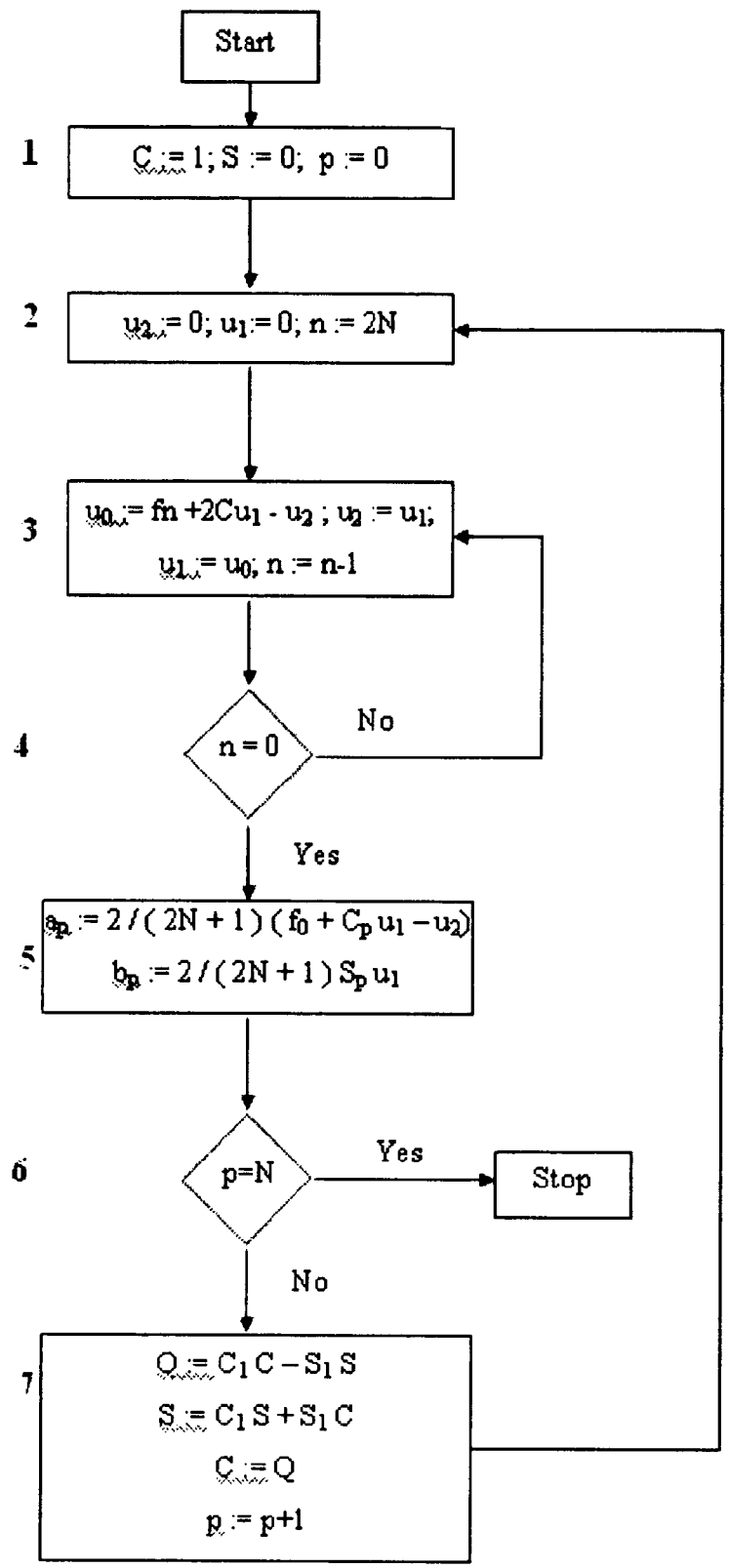
FIG. 19 Flow chart of Fast Fourier Transform used in the present method.

Replace p+1 by p and repeat step 3.2.
Flow chart of Fast Fourier Transform:
FIG. 19 shows the Flow chart of Fast Fourier Transform. The chart is explained below.

Box 1: The counter p is set to zero. The initial value of S and C are set.
Box 2: $U_{2N+2}=U_{2N+1}=0$ is set in $u_2$ and $u_1$. The counter n is set to 2N.
Box 3: Un is calculated from $U_{n+1}$, $U_{n+2}$, and $f_n$. The counter n is decreased by one.
Box 4: If n=0, $u_1=U_1$, and $u_2=U_2$ so that $a_p$ and $b_p$ may be calculated. If not, box 3 must be repeated.
Box 5: $a_p$ and $b_p$ are calculated along with p.
Box 6: If p=N, the problem is done. If not, must be calculating for next p.
Box 7: Calculate S and C for next value of p. Also step counter p up by one. Repeat with box 2.

Correction of Results of Power Spectral Analysis in the Presence of Artifacts and Ectopic Beats.

Besides treatment of artifacts and ectopic beats on the stage of data preparation based on the method of Chireikin, L. V. Shurygin D. Ya., and Labutin V. K., an additional complementary method was employed, so that the combined methods work to increase precision of HRV analysis in the presence of artifacts and ectopic beats. The additional method constitutes correction of results of power spectral analysis in the presence of abnormal beat signals. The following frequency subranges are involved in spectral analysis and in the procedure for correction of results:

Low frequency 2: 0.033-0.07 Hz;
Low frequency 1: 0.07-0.15 Hz;
High frequency: 0.15-0.5 Hz;
Very high frequency: 0.5-1.0 Hz.

The values of the power in HF, LF1 and LF2 can be adjusted depending on the obtained power in the frequency range 0.5-1.0 Hz. If this obtained value in the VHF range exceeds 3,000 ms$^2$, then the obtained power values in the lower frequency ranges are replaced with smaller values assigned according to the principle outlined in the table below:

| Obtained value of VHF, ms$^2$ | Corrections made |
| --- | --- |
| <3,000 | none |
| From 3,000 to 5,000 | value of HF is reduced |
| From 5,000 to 8,000 | Values of HF and LF1 are reduced |
| >8,000 | Values of HF, LF1, and LF2 are reduced |

The method significantly increases the reliability of HRV assessment in the presence of artifacts and ectopic beats.

Algorithm for Clusterization of the Relationship between SNS and PSNS

Overview of the Algorithm:

Methodological basis used for developing the algorithm of clusterization is frame approach, introduced by Marvin Minsky in 1974 (A Framework for Representing Knowledge. MIT-AI Laboratory Memo 306, June, 1974.) The frame is defined as having two components The notion of frame was proposed to denote a structure for interpreting information. Frames represent simple stereotypical situations by clustering all relevant information for these situations together. Frames are composed of two components: declarative and procedural. The declarative component of frame defines an array of slots; each of which can be filled with specific information. The procedural component of frame determines compatibility of the frame with the rest of the incoming data and defines a set of further procedures. The frame approach allowed us to combine arrays of values of all HRV parameters in the algorithm by using the concept of a stereotypical situation.

In order to represent the general structure of the algorithm, we will first define its main constituents and principles of functioning of separate structural elements.

Figure 20:
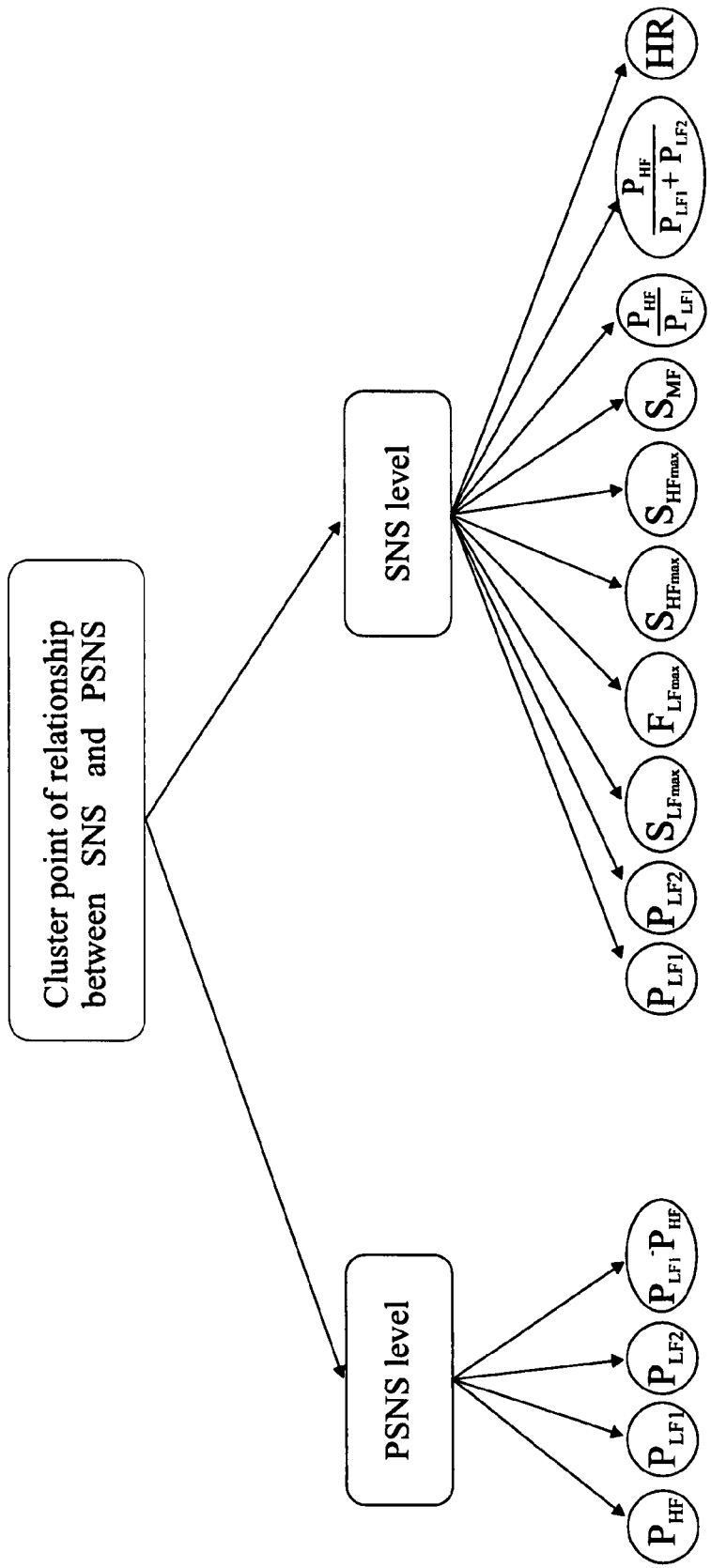
FIG. 20 Schematic representation of semantic network of parameters used in clusterization. Parameters joined by arcs are semantically related parameters connected by the logical symbol "AND". Relationship of parameters of the same level not joined by arcs is defined by the logical symbol "OR." Arrows indicate hierarchical relationship between parameters. Parameters in shaded boxes are top-level parameters; parameters in white boxes are terminal parameters.

Set of Parameters:

The purpose of the method is to find the distribution of intensities of PSNS and SNS. It seems most appropriate to represent the distribution with the coordinate system, where the x-axis would correspond to the intensity of PSNS band, while the y-axis would correspond to the intensity of the SNS band, as shown in FIG. 5. The most convenient was clusterization of each of the above PSNS and SNS parameters into 9 possible gradations, or frames: from −4 to +4. A negative reference value indicates a decreased (lower than average) intensity of PSNS or SNS while a positive value indicates an increase in the activity of either PSNS or SNS bands. FIG. 20 shows Cluster Point reflecting the balance of PSNS and SNS intensities. PSNS value is the x-coordinate, SNS value is the y-coordinate of the point. In this example, PSNS value is 1, SNS value is 2, so SNS intensity slightly predominates.

The objective of the method is to find a point in the coordinate system that reflects the balance of intensities of PSNS and SNS, the point is also called the cluster point.

Analysis of the values of each parameter allows us to determine the value of the principal target parameter—final cluster point of coordinates with PSNS on the horizontal axis and SNS on the vertical axis. The semantic network used in the proposed method is depicted in FIG. 20. All parameters are combined into a hierarchical structure that represents a semantic network. Parameters joined by arcs are semantically related, arrows indicate hierarchical relationship between parameters. All parameters of the semantic network are divided into two categories: main (or terminal) and top level (or derivative). Parameters joined by logical symbol "AND" are grouped on the picture by the arcs. Relationship between parameters or groups of parameters not connected by the arcs is defined by the logical symbol "OR".

Top Level Parameters:

The top level parameters, which are represented on FIG. 20 by rectangles, comprise PSNS cluster value and SNS cluster value. The goal of clusterization is to find the point of balance of PSNS and SNS, or the relationship between intensities of PSNS and SNS during the test.

Figure 21:
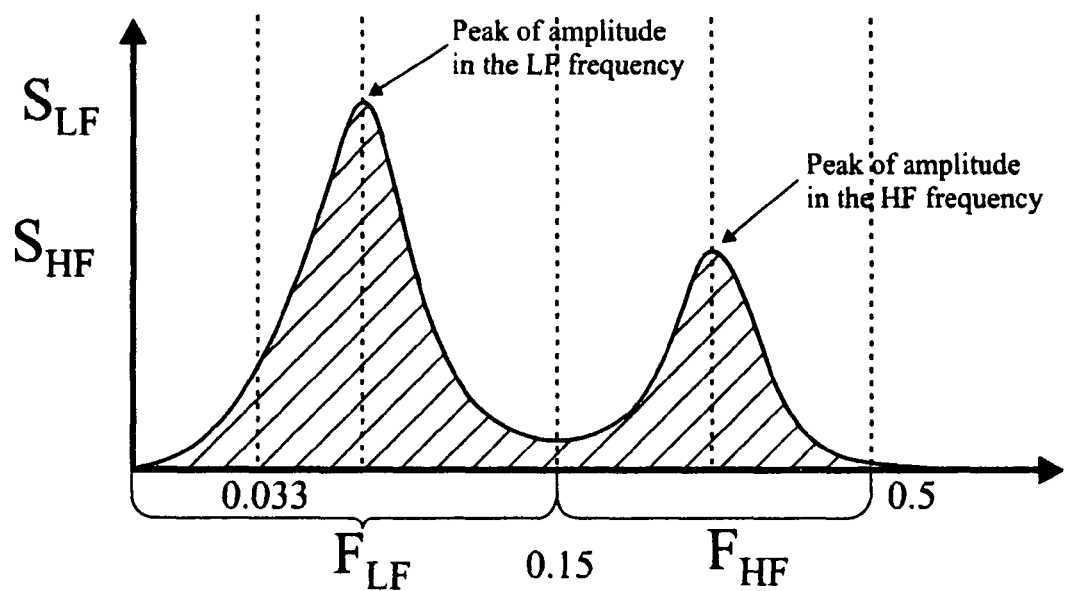
FIG. 21 Graph of power spectrum that reflects distribution of intensities in the HF and LF frequency ranges.

Terminal Parameters:

The terminal parameters of the semantic network, used in the present algorithm, which are represented in FIG. 21 as circles or ovals, are given below.

For PSNS frequency there are four terminal parameters: $P_{HF}$, $P_{LF_1}$, $P_{LF_2}$, $P_{LF_1} - P_{HF}$.

PHF—Power of spectral function in the HF band;
$P_{LF_1}$—Power of spectral function in the $LF_1$ frequency band;
$P_{LF_2}$—Power of spectral function in the $LF_2$ frequency band;
$P_{LF_1} - P_{HF}$—Difference between power of spectral function in the $LF_1$ frequency band and HF frequency band.

For SNS frequency there are ten terminal parameters: $S_{LF}$, $F_{LF\ max}$, $S_{HF\ max}$, $F_{HF\ max}$, $S_{MF\ max}$, $P_{HF}/P_{LF_1}$, $P_{HF}/(P_{LF_1} + P_{LF_2})$.

$P_{LF_1}$—Power of spectral function in the $LF_1$ frequency band;
$P_{LF_2}$—Power of spectral function in the $LF_2$ frequency band;
$S_{LF\ max}$—Peak of amplitude of spectral function in the LF band;
$F_{LF\ max}$—Maximum frequency value of spectral function in the LF band;
$S_{HF}$—Peak of amplitude of spectral function in the HF band;
$F_{HF\ max}$—Maximum frequency value of spectral function in the HF band;
$S_{MF\ max}$—Peak of amplitude of spectral function in the MF band;
$P_{HF}/P_{LF_1}$—Ratio of power of the spectral function in the HF band to power in the $LF_1$ band;
$P_{HF}/(P_{LF_1} + P_{LF_2})$—Ratio of power of the spectral function in the HF band to the power in the low frequency band ($_{LF_1 + LF_2}$).
HR—Heart Rate For convenience of mathematical operation, the present method subsets the range of values of three main parameters: $P_{HF}$, $P_{LF1}$ and $P_{LF2}$ into 30 subranges and assigns values from 1 to 30 to each subrange. For example, the subranges for $P_{HF}$ are the subrange 99999-12000 msec$^2$, 12000 msec$^2$ -11000 msec$^2$; 11000 msec$^2$ -9000 msec$^2$; 9000 msec$^2$-7800 msec$^2$ etc. Subsetting into 30 subranges is based on non-linear scale of exponential type that has been empirically derived.

Figure 22:
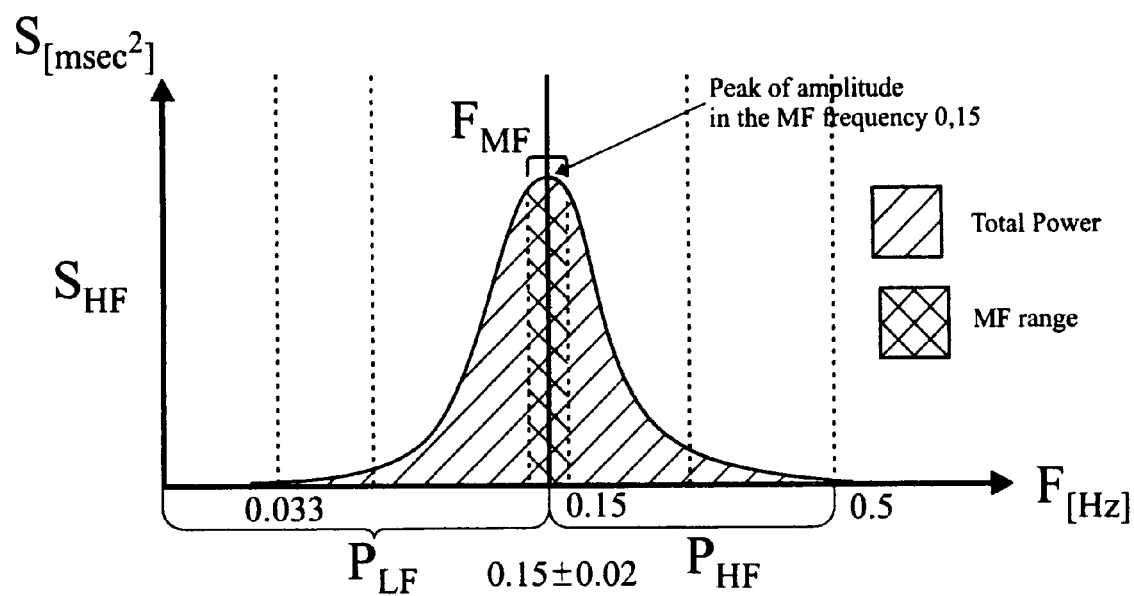
FIG. 22 Graph of power spectrum with peak in the MF frequency range.

Processing of terminal parameters in the method is further described. FIG. 22 represents a graph of the power spectrum that we use in the present method. The graph shows LF and HF frequency bands. The peak of amplitude closer to the left of the spectrum indicates the intensity of LF band; the peak on the right of the spectrum indicates the intensity of HF band. When there is more than one peak, the amplitude of the peak and the total power under the peak will determine whether HF or LF is predominant. It is important which harmonic or group of harmonics correspond to the peak of amplitude in HF or LF band, and at what value of frequency this peak occurs.

Figure 23:
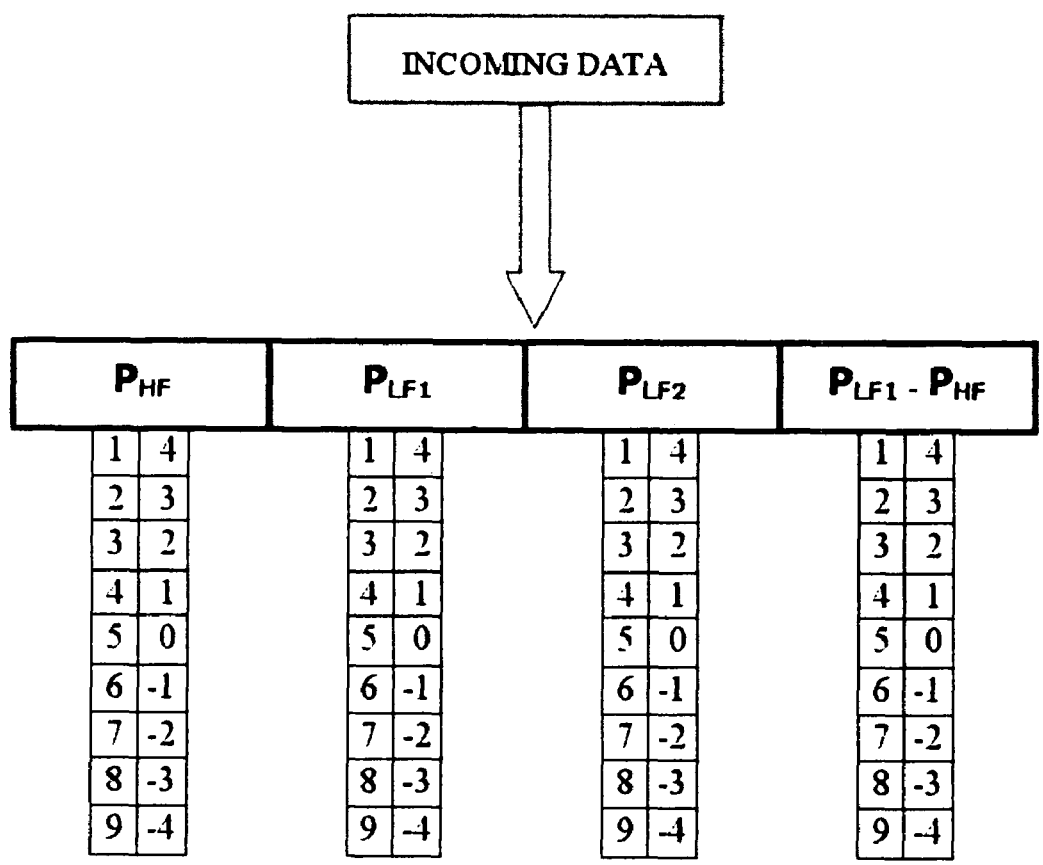
FIG. 23 Diagram of the frame aggregate for recognition of PSNS cluster point.

For a more precise analysis, a special case of mid-frequency peak is also considered. If the peak of amplitude falls between the HF and LF bands—in the range from 0.15±0.02 Hz, then the MF parameter is introduced in the computational process. FIG. 23 shows a case when there is a distinct peak in the MF frequency range.

For a more convenient operation of the algorithm and to make our HRV analysis more precise we divided LF in two sub ranges: $LF_1$ (0.07-0.15) and $LF_2$ (0.04-0.07). This, according to various publications on HRV, also agrees with the assignment of different physiological parameters to each of the two sub ranges.

Values of parameters in a semantic network:

Values of top level (derivative) parameters are sets of concepts that make up the core content of a parameter; values of terminal parameters are domains of data.

Aggregates of Frames:

As mentioned above, a frame is a structure for knowledge representation that has two components: declarative and procedural. Declarative component contains descriptions of all possible situations. The procedural component contains an algorithm for evaluating compatibility of incoming data with one of the frames; this component defines a set of further procedures.

Declarative component (DC) of frames is stereotypical situations that appear during analysis of parameters joined by the logical symbol "AND" shown as arcs in FIG. 20.

FIG. 23 represents the Frame aggregate for recognition of PSNS cluster point. For recognition of PSNS cluster point, the analyzed parameters are $P_{HF}$, $P_{LF_1}$, $P_{LF_2}$, $P_{LF_1}$-$P_{HF}$. As a rule, an aggregated description of a frame is an expression that represents one of the values of a corresponding top level (derivative) parameter. For example, in case of HF cluster point recognition, it is one of the possible points from −4 to 4 on the coordinate system of HF. Then the set of original data, reflecting the obtained HF value is the realization of the frame, recognized by the procedural components (PC) of the analyzed set.

Figure 25:
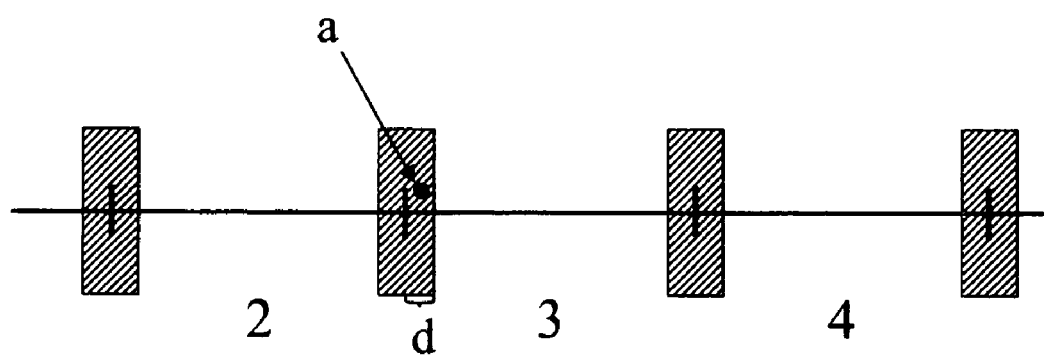
FIG. 25 Principle of "fuzzy" borders, if a value falls within a distance d from the border (within the shaded area), it can be considered to belong to both intervals. For example, a value falling at a point a can be attributed to interval 3 or to interval 2 depending on other recognized values.

For recognition of SNS cluster points, the system must analyze the following parameters: $S_{LF}$, $F_{LF}$, $S_{HF}$, $F_{HF}$, $S_{MF}$, $P_{HF}/P_{LF_1}$, $P_{HF}/(P_{LF_1}+P_{LF_2})$ and HR, and as a result the algorithm selects an LF value—a point from −4 to 4 on the system of coordinates, where the data for the test falls. Frame aggregate for recognition of SNS cluster point is shown in FIG. 25.

Structure and functioning of the algorithm for recognition of frame aggregates

Figure 24:
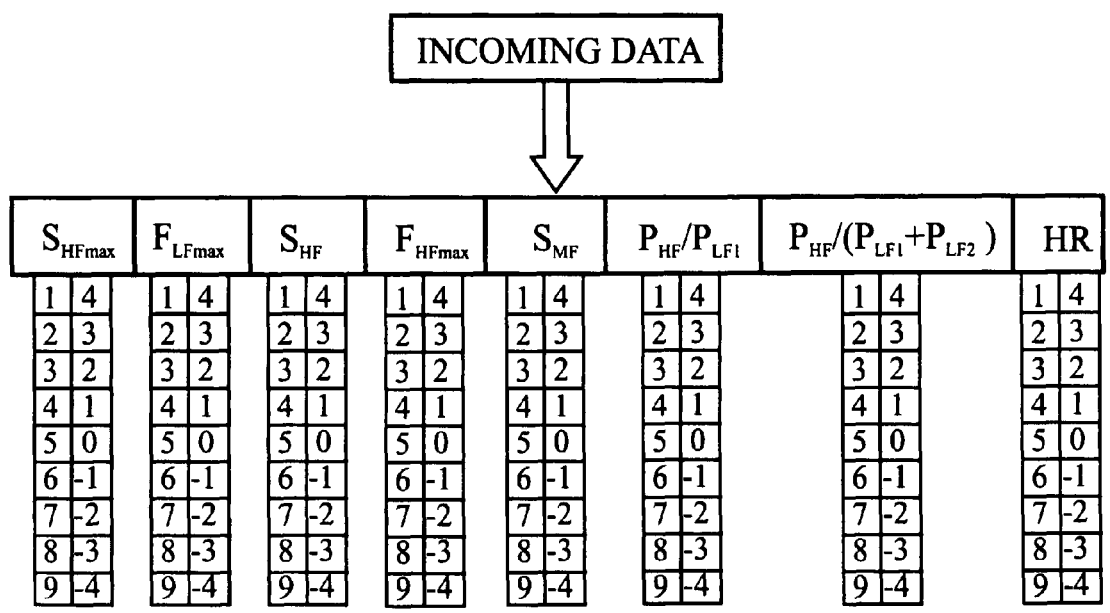
FIG. 24 Shows the frame aggregate for recognition of SNS cluster point.

Structure of the algorithm:

There are two separate branches of the algorithm:

1 the branch that recognizes PSNS values, or Frame aggregate for recognition of PSNS cluster point (FIG. 24).

2 the branch that recognizes SNS values, or Frame aggregate for recognition of SNS cluster point (FIG. 25).

One of the characteristics of using frame representations is the structure of residential part of the recognition mechanism, which is common for each of the separate frame aggregates. In the proposed method the residential part is also common for SNS and PSNS frame aggregates.

Conformity Slots

The algorithm finds the most appropriate value (point on the horizontal axis) for the PSNS parameter, and the most appropriate value (point on the vertical axis) for the SNS parameter. The role of conformity slots is to determine whether the initial value selected by the algorithm is appropriate, or to find a most appropriate value. In other words, the task of conformity slots is to "decide" whether the value corresponds to (conforms with) a certain point on the PSNS coordinate axis or not. If it does not, conformity slots should select a most appropriate point. Each of the 9 values (frames) of a parameter has their own sub domains, so both PSNS parameter and SNS parameter each have 9 sub domains. If input falls into one of the sub domains, it is marked by a "Flag," or is assigned a value of 1. Ideally, the direct assignment of a value, or selection of a point, would be sufficient in analysis. However, dealing with real data requires an additional part of the algorithm—introduction of conformity slots.

In order to illustrate the role of conformity slots, consider an example of recognition of HF parameter. In this case, the ideal situation would be if all of the 4 parameters in the HF algorithm fall, for instance, into the value of 7 (−2 on the axis), then the recognition process would be completed, and the point −2 on the PSNS axis would be selected. In reality, they can often fall into different value domains, e.g. the $P_{HF}$ parameter falls into the $7^{th}$ sub domain, the $P_{LF_1}$—into the $6^{th}$, $P_{LF_2}$—into the $8^{th}$, $P_{LF_1}$-$P_{HF}$—into the $9^{th}$. Thus it is necessary to further analyze these situations. This is when conformity slots come into action. In case they fall into different sub domains, i.e. do not match, algorithm should analyze all their values for conformity and to determine which of them is most appropriate. Let us assume that all the 4 parameters describing a certain test fall into different frames. The further analysis is then performed as follows: the first obtained value is analyzed for conformity. If it is rejected, the second value is analyzed etc. until the algorithm finds a most appropriate value.

The same process of value recognition is used in the SNS algorithm. PSNS algorithm determines the position on the x (PSNS) axis, while the SNS algorithm determines the position on the y (SNS) values. As a result of work of the two branches of the algorithm a point in the PSNS/SNS system of coordinates is found, this point reflects the relationship between the intensities of PSNS and SNS (FIG. 5).

Functioning of the Algorithm (Mechanism of Recognition of PSNS and SNS Cluster Point The properties of the frame recognition mechanisms are mainly determined by the environment where the recognition takes place.

The mechanism for recognition of frame aggregates is composed of 3 main constituents:

1 Residential part—(frame switch);
2 Procedural component of each frame;
3 "Demons". "Demons" are intended mainly for addressing a new frame-candidate independently of a rejected frame. They have distinguishing markers, pointing directly to other frames and not through the frame switch. There are two main types of demons: CONTDEM—demon with continuation; STOPDEM—demon with stop.

If the data fall on the border line of a certain domain of a frame, the demon with continuation (CONTDEM) is activated. The purpose of the CONTDEM is to determine if the data should be assigned into the $2^{nd}$ or $3^{rd}$ frame, and the principle of "fuzzy" borders is used (FIG. 26) If a value falls within a distance d from the border (within the shaded area), it can be considered to belong to both intervals. For example, a value falling at a point a can be attributed to interval 3 or to interval 2 depending on other recognized values.

Figure 27:
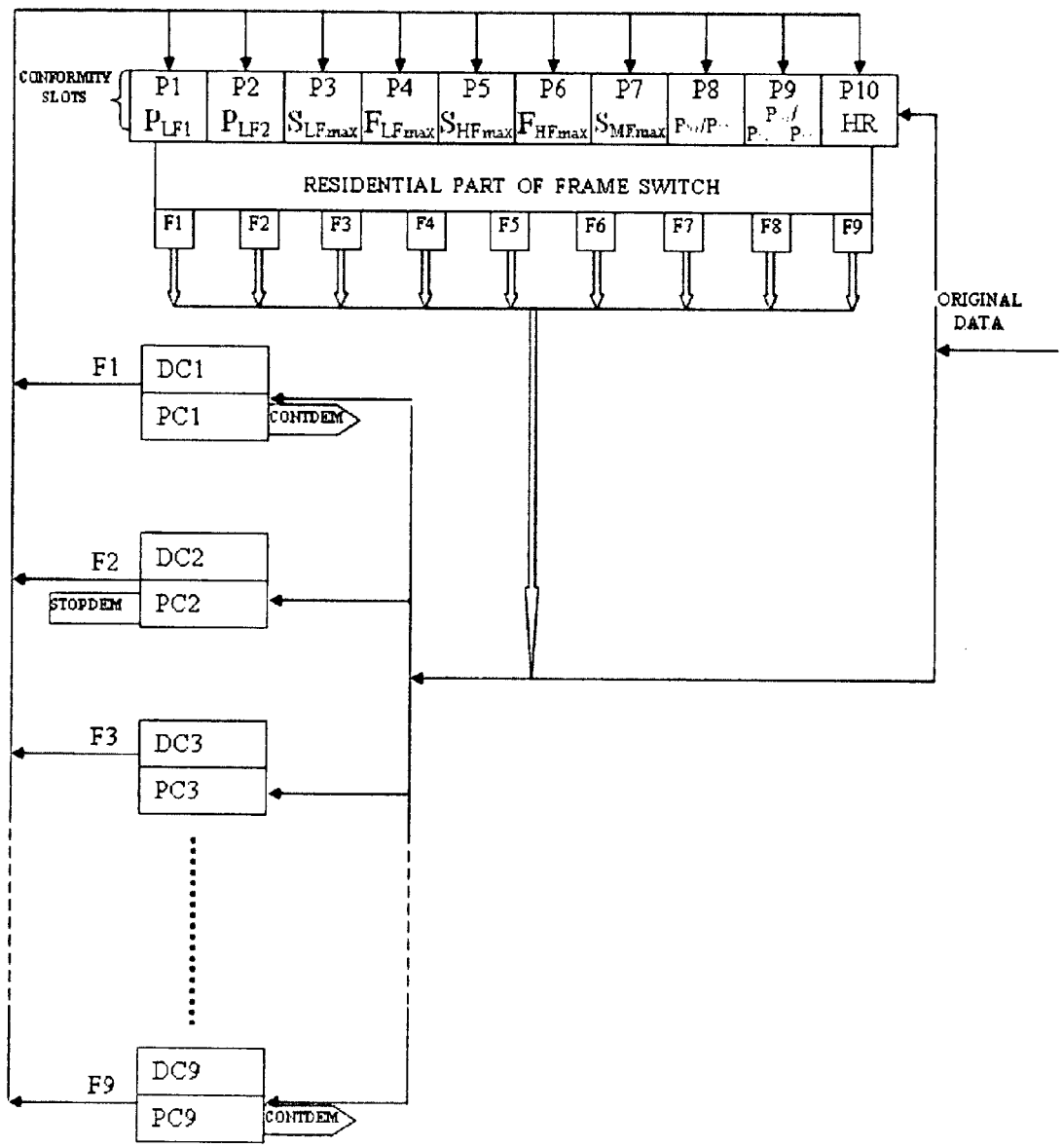
FIG. 27 Scheme showing general structure of the algorithm for SNS cluster point recognition, where abbreviations and symbols are the same as in FIG. 26.

The general structure and mechanism for HF cluster point recognition is shown in FIG. 27. If the data definitely fall into, for instance, the $3^{rd}$ sub domain, then STOPDEM is activated since there is no ambiguity.

If data do not fall into the same sub domain, then an additional mechanism switches on—this mechanism is shown in the lower part of FIG. 27. The declarative component of a frame is analyzed, then the procedural component determines the next procedure depending on the activated demon.

STOPDEM does not mean the process is completely stopped, it means that the procedural component is not able to proceed with further analysis.

In the scheme of the recognition mechanism in FIG. 27 the black arrows stand for information signals, while the white contoured arrows show up-down control.

Figure 28:
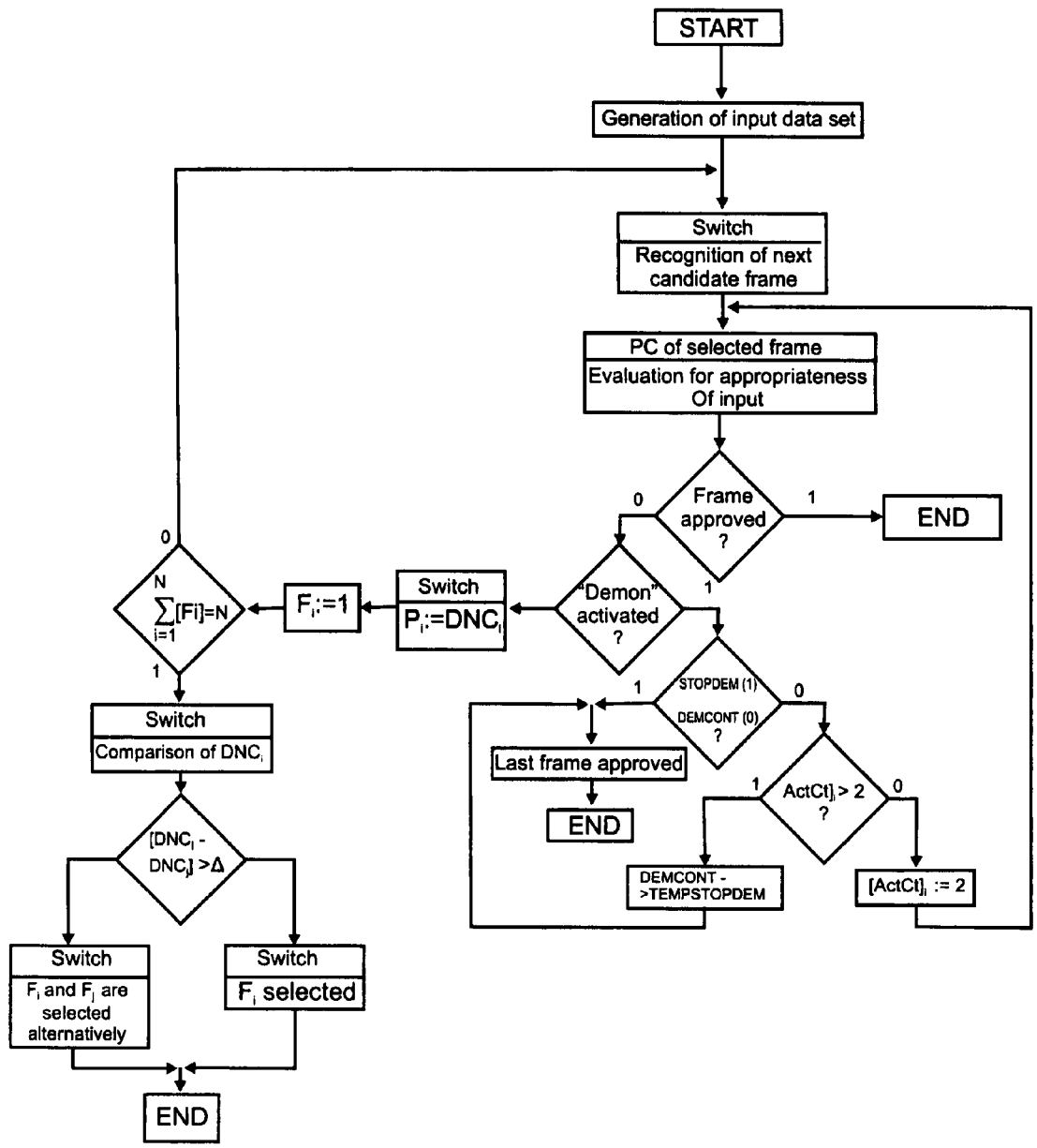
FIG. 28 Diagram describing an algorithm for recognition of the final cluster point (Common for PSNS and SNS frame aggregates)

The general structure and mechanism for SNS cluster point recognition is similar to the one just described and is shown in FIG. 28. The algorithm is essentially the same for SNS and PSNS, except for it works with different sets of data.

Figure 29:
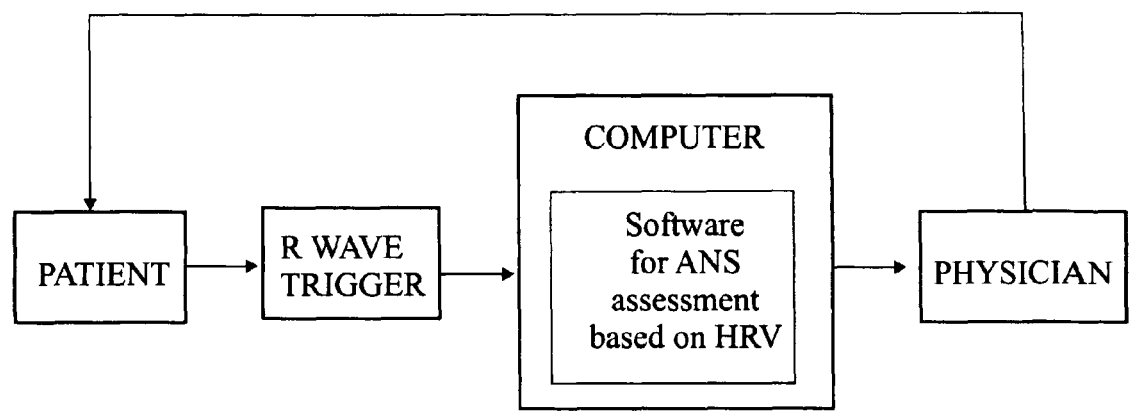
FIG. 29 Schematic representation of the system for implementation of the present method of ANS assessment based on HRV analysis.

In more detail, the recognition mechanism can be represented as shown in FIG. 29. This scheme reflects the functioning of the cluster point recognition mechanism, and this mechanism is the same for PSNS recognition and for SNS recognition. The original generated set of data is analyzed for four parameters ($HF$, $LF_1$, $LF_2$ and $LF_1 - HF$) in case of PSNS cluster point recognition, and 10 parameters ($LF_1$, $LF_2$, $S_{LF}$, $F_{LF}$, $S_{HF}$, $F_{HF}$, $S_{MF}$, $P_{HF}/P_{LF_1}$, $P_{HF}/(P_{LF_1}+P_{LF_2})$, HR) in case of SNS cluster point recognition.

1. Set of original data related to a certain parameter to be recognized is supplied to the input of the residential part of the frame switch. The frame switch uses its default knowledge about frame recognition to connect the input data set to a candidate frame. It analyzes incoming data for conformity to each candidate frame based on algebraic set of operations, so that the principle of proximity of the values to the frame domains is used for analysis.
2. Procedural component of a given frame is then switched on. It evaluates incoming data for conformity to the frame. If it finds that the data conforms to the frame, the process of recognition is stopped. If a frame is not chosen, then the algorithm checks whether the STOPDEM or CONTDEM is activated. In case a proposed frame value is rejected, there are two alternatives.
a) The first alternative is activation of a corresponding "demon" if present, which can lead either to selection of a new frame (for continuation demons CONTDEM) or to ending the recognition process (for stop demons STOPDEM). In case a stop demon is activated, the frame is considered to be recognized as the one that the demon points to.

There is one exception when the recognition process stops while temporary stop demon is activated (TEMPSTOPDEM). This happens when CONTDEM creates an infinite loop for two frames: CONTDEM counts the number of activations, and when the count $ActCt_i = 2$ (i-th demon), the corresponding CONTDEM becomes TEMPSTOPDEM. Then this process is temporarily stopped while the algorithm performs other operations. In this case two frames have the same degree of conformity and the recognized parameter is assigned both values.
b) The second alternative in case of a frame rejection is connecting the data set to the frame switch again, this time the previously rejected frame will not be considered (the flag, or marker of this frame $F_i$ has been assigned the value of 1). It is necessary to note that the switch will "remember" the degree of non-conformity (DNC) of a rejected frame in the slot $P_i$.

The recognition process continues until one of the frames is accepted as appropriate. If all of the given conformity slots of possible frames are rejected the algorithm will return to the frame switch again, which will choose a frame with the least degree of non-conformity. If there are frames (Fi and Fj) with the same degree of non-conformity in the range of significant difference, they will be both considered a result of the recognition process.

So the algorithm of functioning of frame aggregate recognition mechanisms allows us in any case to produce a description of the recognized frames in the least close to the actual one, considering knowledge represented in the system, and fundamentally excludes the possibility of producing an illogical result. Having analyzed these 4 parameters in case of PSNS recognition or 10 parameters in case of SNS recognition, one of the 9 values can be obtained.

Figure 26:
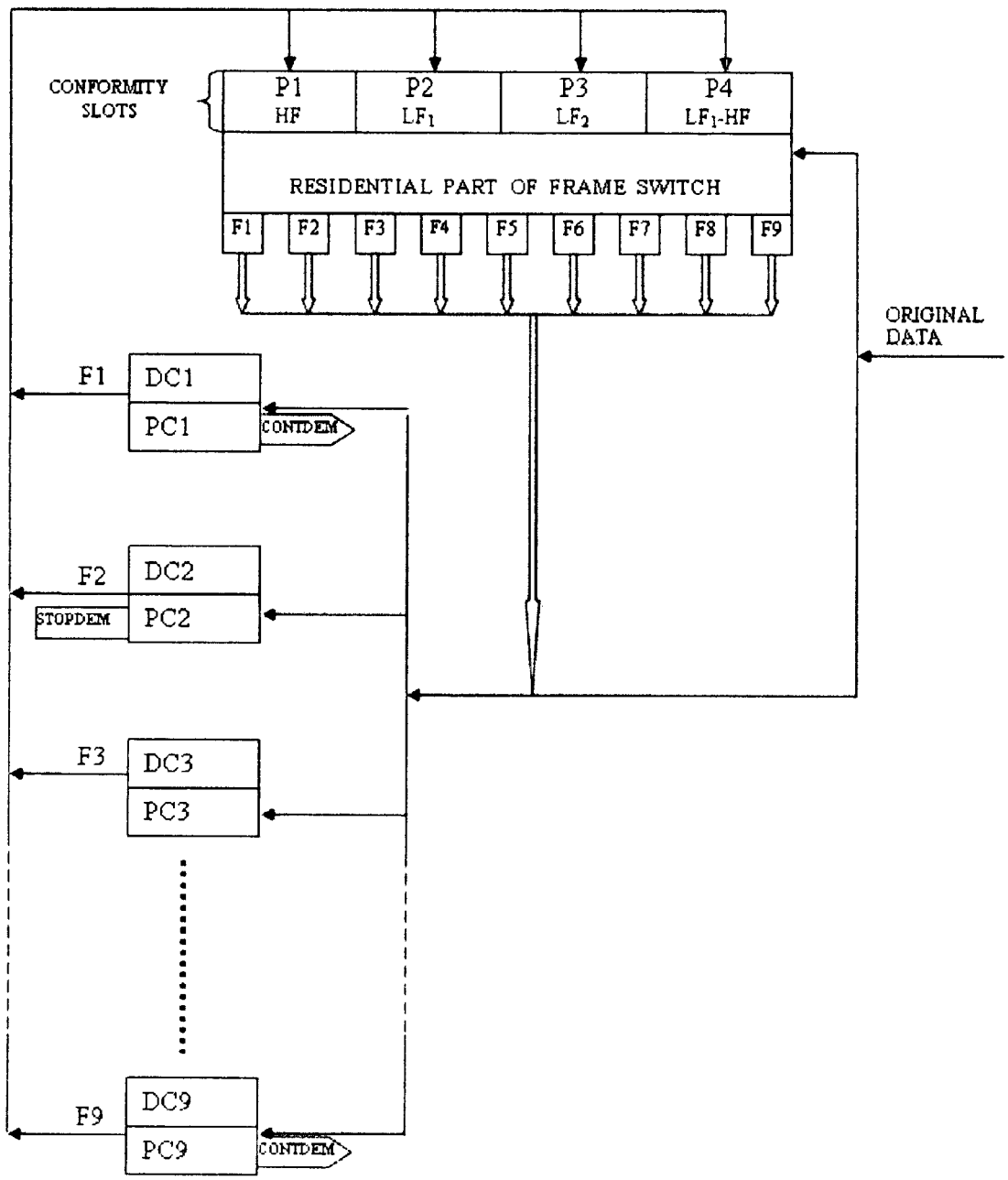
FIG. 26 Scheme showing general structure of the algorithm for PSNS cluster point recognition, with the following symbols and abbreviations: P—parameter, F—frame, DC—declarative component, PC procedural component, CONTDEM—continuation demon, STOPDEM—stop demon, black thin arrow—information signals, think white arrow with black contour—up-down control.

Principles of recognition of the procedural components of frames
1. Each condition or domain of a parameter, recorded in the declarative component of a frame, is evaluated for conformity to a given frame, using besides a strict assignment of domains the principle of "fuzzy" borders, or falling onto the borderline. The principle is illustrated in FIG. 26.
2. The conclusion about conformity of the analyzed parameter is expressed by assigning "1" to the corresponding conformity slot of the parameter.
3. One of the methods of evaluation of conformity is interrelated analysis of values of two functionally connected parameters in the case when one of them does not fall into the domain for a given frame. All the functions in the proposed method are interrelated.
4. In case of non-conformity of a declarative component of a frame the algorithm uses principle of direct transition to another frame by using CONTDEM and STOPDEM. In this situation CONTDEM is used in cases when the non-conformity is not explicit, while STOPDEM is used when the non-conformity is dramatic, which indicates that the value should be related to another frame.
5. When procedural component detects a non-conformity but does not point to another frame, the responsibilities for the decision to be made are passed from the procedural component to the frame switch.
6. In cases, when conditions of a slot are not significant for a given frame, the algorithm uses the principle of filling it the slot automatically (by default).

System for Implementation of ANS Assessment based on HRV Analysis

The method can be implemented in a computer-based system that is schematically represented in FIG. 29. Heart beat data are collected from patient by an ECG device that triggers R Waves of each consecutive beat and transmits the R Wave signal to a personal computer. The software program, preinstalled on the computer, analyses variability of the received R Wave signals, i.e. performs heart rate variability analysis. The software transforms results of HRV analysis into the clusterization chart, where activity of parasympathetic system is displayed on the horizontal axis while activity of parasympathetic system—on the vertical axis. The system presents results of the analysis to the user (physician) via a user-friendly interface on the computer screen and allows results storage and other functions for management of patients' data.

Figure 30:
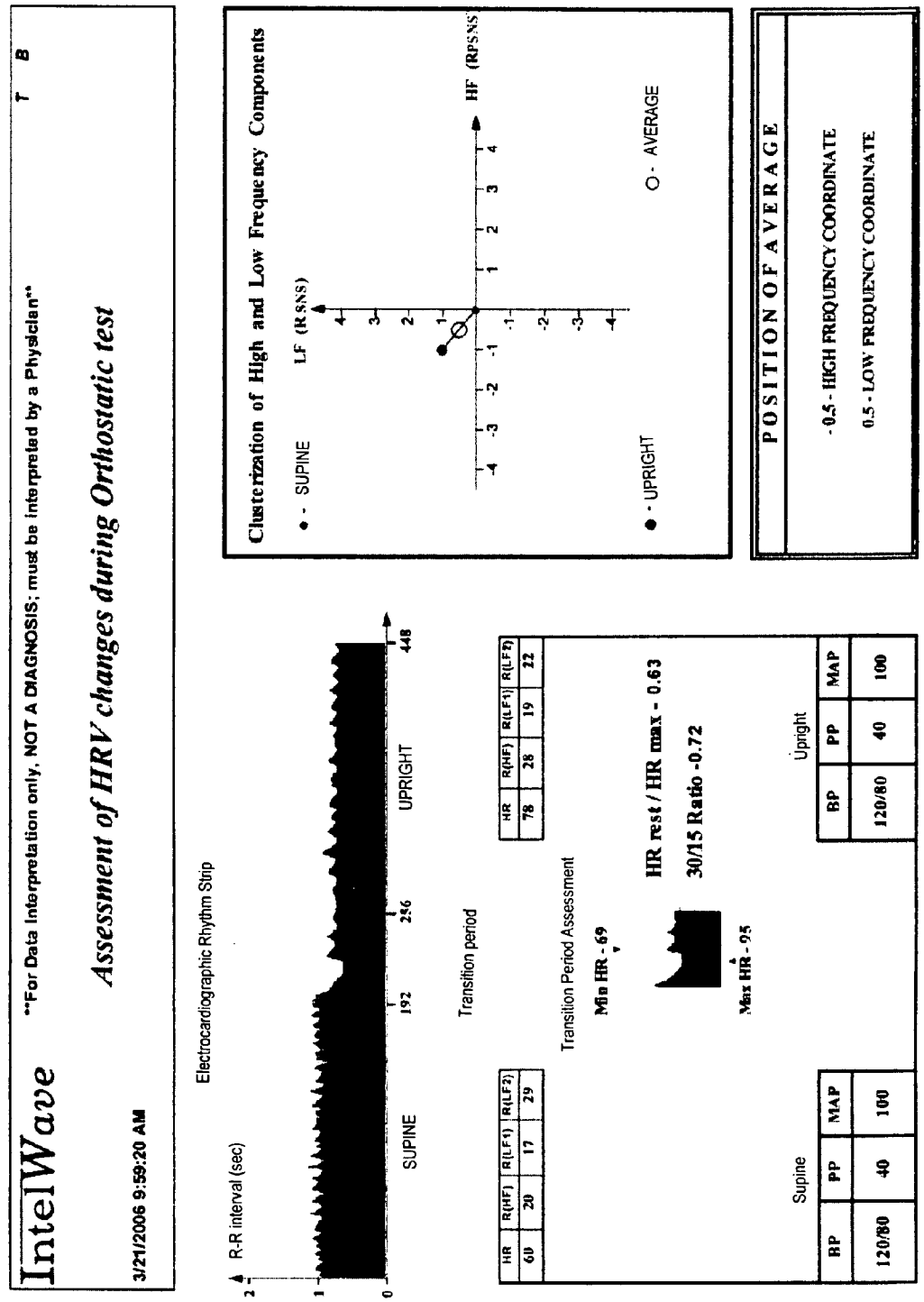
FIG. 30 Sample results printout with ANS screen for an Orthostatic test.
Figure 31:
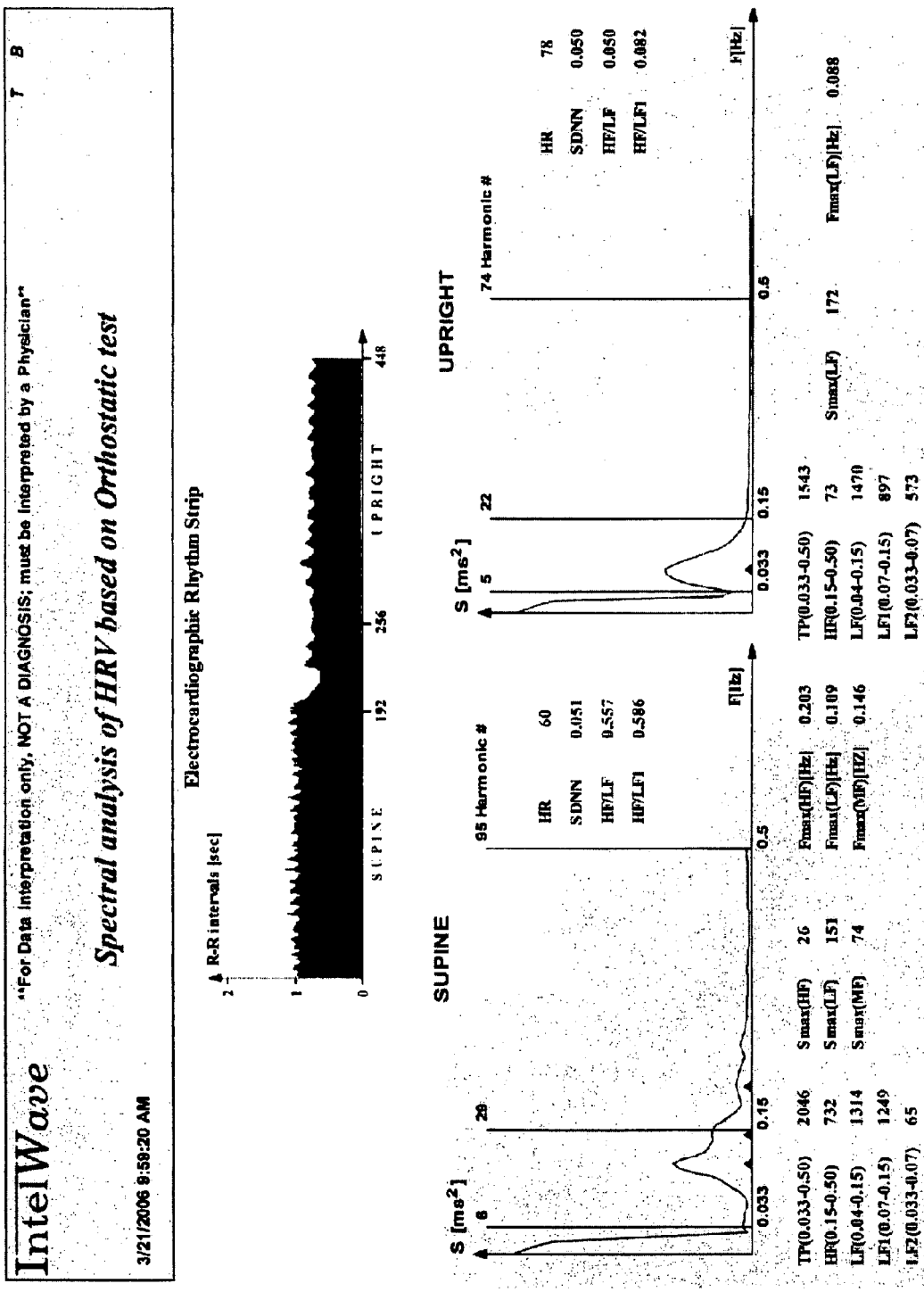
FIG. 31 Sample results printout with spectral analysis screen for an Orthostatic test.
Figure 32:
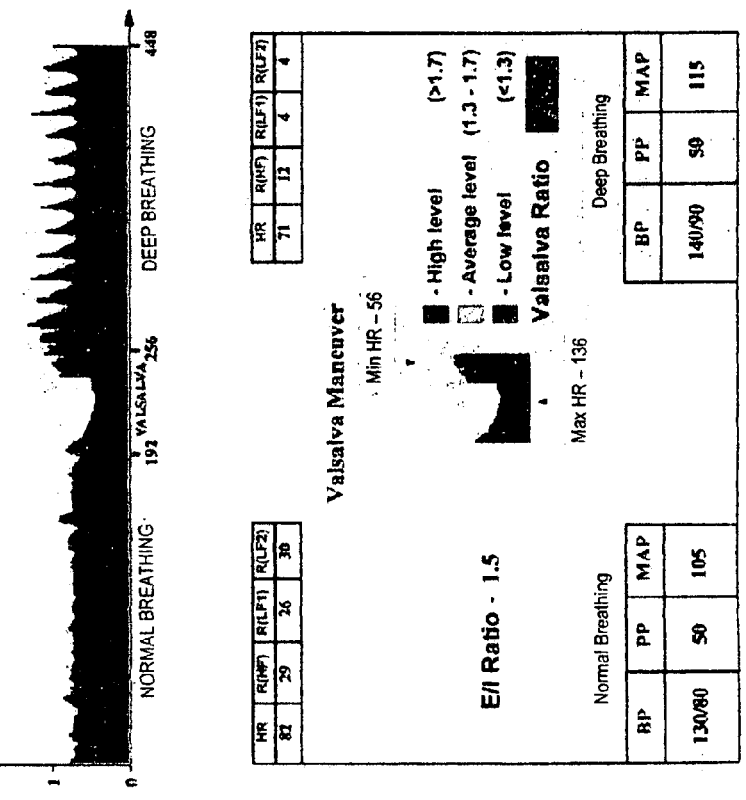
FIG. 32 Sample results printout with ANS screen for a Valsalva test.
Figure 32:
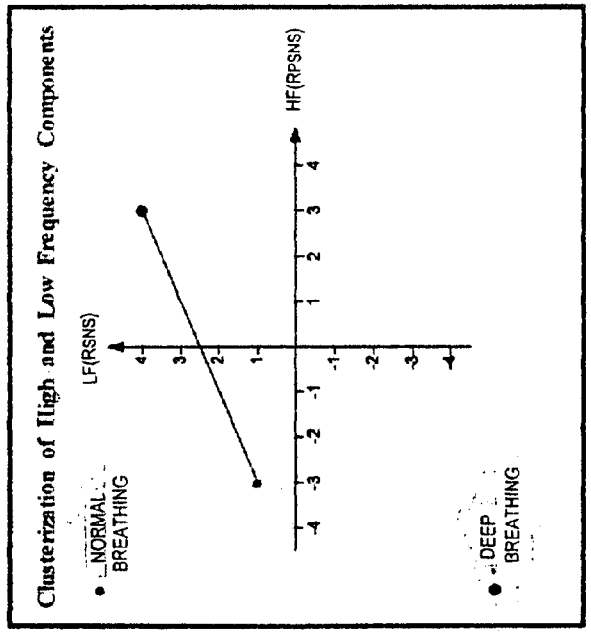
Figure 33:
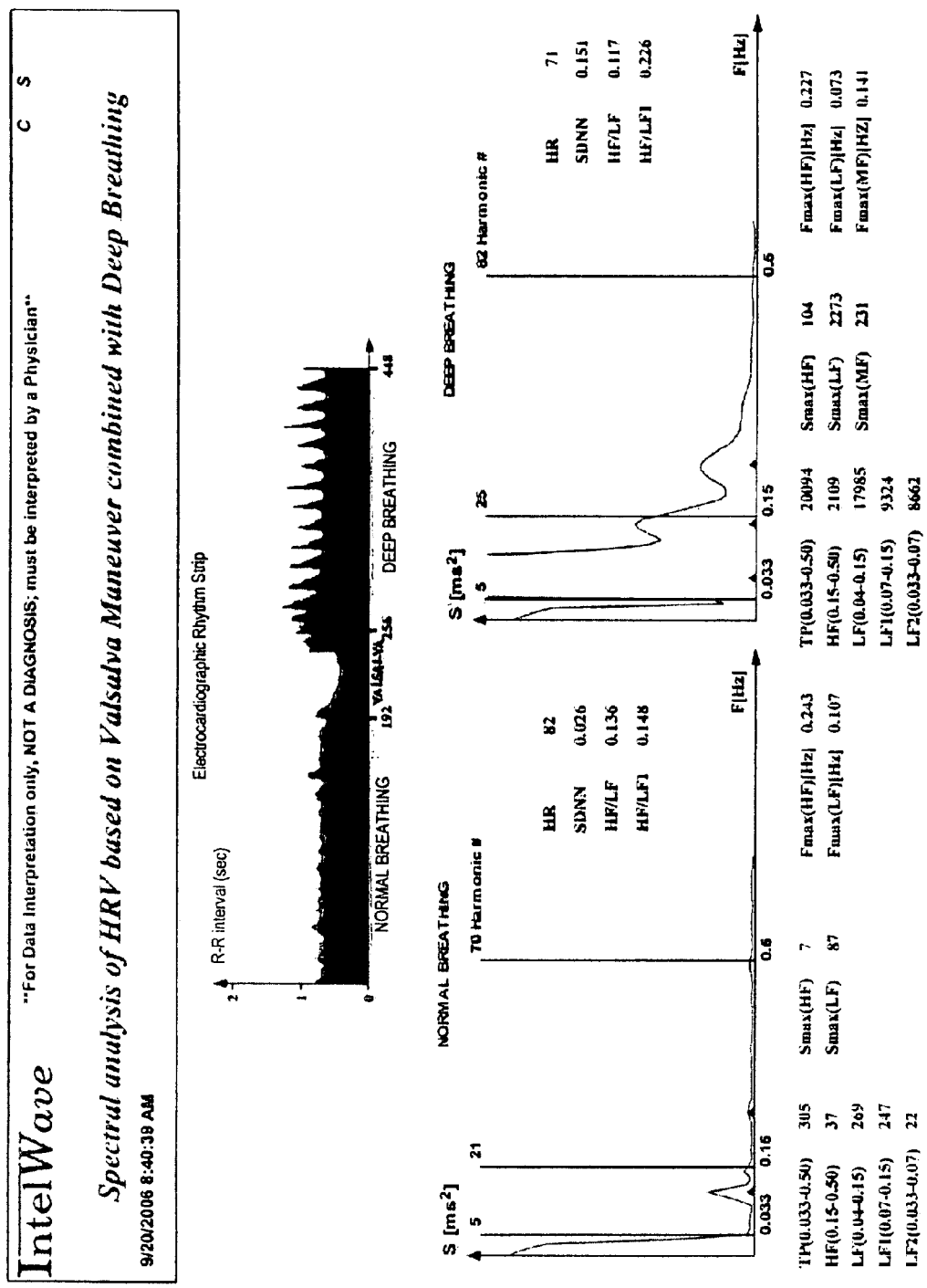
FIG. 33 Sample results printout with spectral analysis screen for a Valsalva test.
Figure 34:
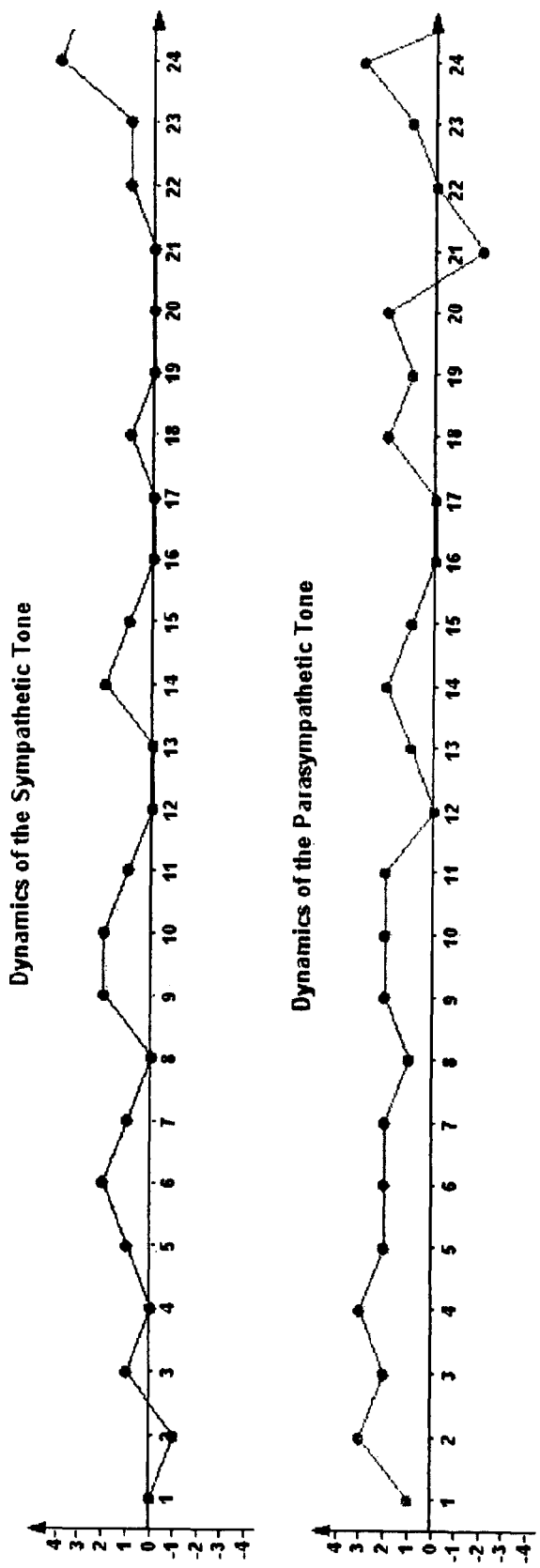
FIG. 34 Sample results printout with ANS screen for a real-time assessment.
Figure 35:
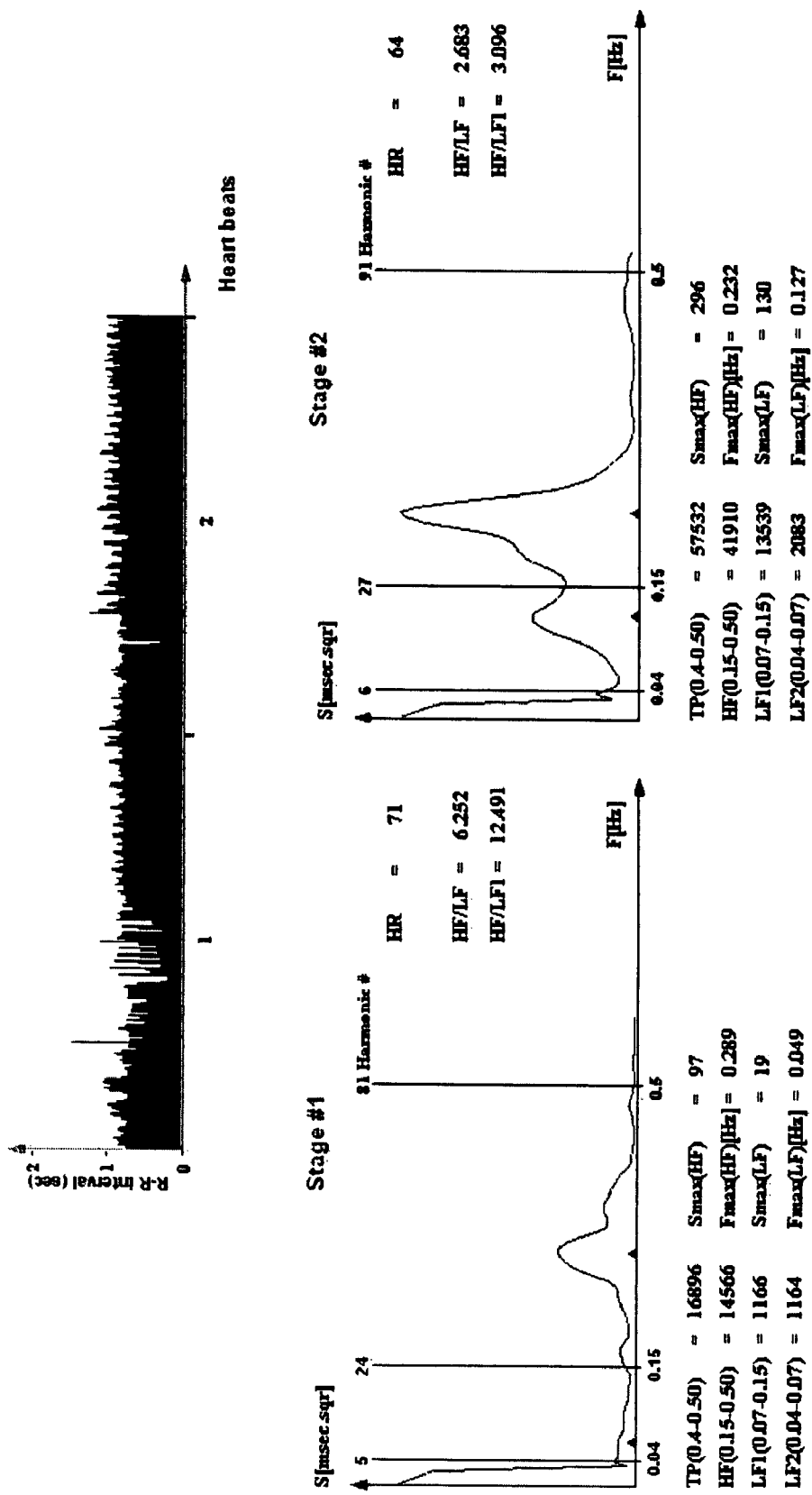
FIG. 35 Sample results printout with Spectral analysis screen for a real-time assessment.

Sample results printouts generated by the system are presented in FIG. 30-35. As shown on the figures, for each test modality, there are two main types of results screens: spectral analysis screen and ANS assessment screen. FIGS. 30 and 31 show screen results for Orthostatic test. FIGS. 32 and 33 show screen results for the Valsalva maneuver combined with deep breathing. FIGS. 34 and 35 show screen results for real-time HRV analysis.

Below are proposed results printouts (that are also displayed on the computer screen) for all test types. Results pages for the orthostatic test discussed herein are Cluster Analysis page for orthotest and spectrum page for orthotest. Results pages for the Valsalva maneuver combined with deep breathing test are cluster analysis page for the Valsalva test and spectrum page for the Valsalva test. Result for Real-time HRV analysis are cluster graph page for real-time HRV analysis and Spectrum page for Real-time HRV analysis.

FIG. 30 shows proposed computer screen printout of ANS analysis page for orthotest results. Cluster analysis page includes the following sections: rhythmographic strip in the upper portion, HRV parameters below the rhythmogram on the left side of the panel, assessment of the lying-to-standing transition period below the HRV parameters, blood pressure related parameters on the bottom, and clusterization chart on the right-hand side.

FIG. 31 shows screen of spectrum page for results of an orthotest. Thus spectrum page includes the following sections: rhythmographic strip in the upper portion, spectral chart for the supine stage of the test on the left side of the panel, spectral chart for the upright stage of the test on the right side of the panel, and HRV parameters below the charts and to the right of each chart. Spectral function shown on the spectrum chart consists of 96 harmonics. Spectral analysis allows one to identify two main components:
Low frequency: 0.033-0.15 Hz.
High frequency: 0.15-0.5 Hz.

The horizontal or X-axis, shows frequency in Hertz. The vertical or Y-axis, shows amplitude of spectral harmonics (S, $msec^2$). The low and high frequency bands can be easily identified on the chart. The vertical lines between different frequency bands show the harmonic for this frequency and an order of the harmonic is written above the line. If present, the maxima of the spectral function are shown by triangles for each range if present. Spectral charts for the Valsalva test (FIG. 33) has a similar format with the difference that on the left side of the panel is the spectral chart for the normal breathing stage of the test is displayed, and the right side of the panel displays the spectral chart for the deep breathing stage of the Valsalva test.

FIG. 32 shows ANS results screen for the Valsalva test, which is in general similar to the format of the ANS screen for orthotest, with features specific to this test type. The middle section of the page contains assessment of the transition period during the Valslava maneuver, which is comprised of a part of rhythmographic strip during this stage, the Valsalva ratio and E/I ratio.

FIG. 33 displays ANS assessment results for real-time HRV analysis that shows dynamics of PSNS and dynamics of SNS on separate charts. Spectrum page for real-time HRV analysis has a similar format to spectrum pages for other test types and displays any two selected consecutive stages.

REFERENCES

1. T. Bigger, N. Rottman. Spectral Analysis of RR Variability. Chapter 19 in Cardiac Arrhythmia—Mechanisms, Diagnosis, and Management, Podrid P J, Kowey P R editors. Baltimore: William & Wilkins, 1995: 280-298.
2. L. Chireikin, D. Shurygin, and V. Labutin, Automatic Analysis of Electrocardiograms (Russian), Nauka, Leningrad, 1977.
3. E. Kazin, A. Riftine. "Automated systems for the complex evaluation of the health and adaptive reserves of the human body." Human Physiology, USSR, 1990, 16(3): 94-99.
4. M. Minsky. A Framework for Representing Knowledge. MIT-AI Laboratory Memo 306, June, 1974.
5. Riftine, Alexander. Clinical Applications and Practical use of Fully Automatic System for Quantitative Assessment of Autonomic Nervous System Condition Based on Heart rate variability Analysis. In *Proceedings of the 18th Annual International Symposium on Man and His Environment in Health and Disease. Special focus: Environmental Aspects of Cardiovascular Disease*. Dallas, Tex., June, 2000.
6. Riftine, Alexander. ANS Assessment as an Indicator of Environmental Pollution Impacts on the Human Body. In *Proceedings of the 23rd Annual International Symposium on Man and His Environment in Health and Disease. Special focus: The Autonomic Nervous System and Its Relationship to Environmental Pollutants Including the Cardiovascular System and Electromagnetic Sensitivity*. Dallas, Tex., June, 2005.
7. Riftine, Alexander. Recognition of physiological states of an individual based on mathematical analysis of heart rate variability. PhD thesis, Glushkov Institute of Cybernetics National Academy of Sciences of Ukraine, Kiev, 1987.
8. Riftine, Alexander. Clusterization of the Relationship between SNS and PSNS activity by Heart Rate Variability Analysis. In *Proceedings of the 33rd International Congress of Electrocardiology*. Cologne, Germany, July, 2006.
9. Riftine, Alexander. New quantification of the relationship between SNS and PSNS activity by heart rate variability analysis. In *Proceedings of General Assembly of Polish Cardiac Society—$1^{st}$ Appointment*. Warsaw, Poland, 2005.
10. N. Rottman, C. Steinman, P. Albrecht, T. Bigger, M. Rolnitzky, L. Fleiss. "Efficient estimation of the heart period power spectrum suitable for physiologic or pharmacologic studies." The American Journal of Cardiology, 1990, 66:1522-1524.
11. Terechtchenko, Larissa, Doronina, Svetlana, Pochinok, Elena and Riftine, Alexander. "Autonomic Tone in Patients with Supraventricular Arrhythmia Associated with Mitral Valve Prolapse in Young Men." Pacing and Clinical Electrophysiology. January 2003, 26: 444-446.
12. D. Zhemaitite. The methodology for automatic analysis of rhythmograms and its clinical applications. PhD thesis, Kaunas, Lithuania, 1972.
13. "Heart rate variability. Standards of measurement, physiologic interpretation, and clinical use. Task Force of the European Society of Cardiology and the North American Society of Pacing and Electrophysiology." European Heart Journal, 1996, 17: 354-381.

What is claimed is:
1. A method for characterizing autonomic nervous system activity of a patient comprising:

(a) acquiring electrocardiographic data from the patient with an electrocardiographic device;
(b) determining from the electrocardiographic data obtained in step (a) a plurality of time intervals between successive R-waves;
(c) analyzing the plurality of time intervals by frequency domain analysis so as to quantitate the following parameters:
i) power of high frequency ($P_{HF}$);
ii) power of low frequency 1 ($P_{LF1}$) (0.07 to 0.15 Hz);
iii) power of low frequency 2 ($P_{LF2}$) (0.033 to 0.07 Hz);
iv) difference between power of low frequency 1 and high frequency ($P_{LF1}$ - $P_{HF}$);
v) maximum amplitude of spectral function in a low frequency band ($S_{LFmax}$);
vi) frequency at a point of maximum amplitude of spectral function in the low frequency band ($F_{LFmax}$);
vii) maximum amplitude of spectral function in a high frequency band ($S_{HFmax}$);
viii) frequency at a point of maximum amplitude of spectral function in the high frequency band ($F_{HFmax}$);
ix) ratio of power of high frequency to power of low frequency 1, ($P_{HF}/P_{LF1}$) ;
x) ratio of power of high frequency to power of low frequency (sum of powers of low frequency 1 and low frequency 2), ($P_{HF}/(P_{LF1} + P_{LF2})$);
xi) heart rate (HR);
and, if a spectral peak falls in the range of a middle frequency band,
xii) ($S_{MF}$) maximum amplitude of spectral function in a middle frequency band; and
(d) applying a clusterization algorithm to the parameter values quantitated in step (c) so as to determine two further parameters, one of which correlates with sympathetic nervous system activity and the other of which correlates with parasympathetic nervous system activity, wherein parasympathetic nervous system activity is determined by applying the clusterization algorithm to parameters (c)(i) to (c)(iv) and wherein sympathetic nervous system activity is determined by applying the clusterization algorithm to parameters (c)(ii), (c)(iii), and (c)(v) to (c)(xii), so as to thereby characterize the autonomic nervous system activity of the patient.

2. The method of claim 1, wherein the high frequency is 0.15 to 0.5 Hz.

3. The method of claim 1, wherein the value of $P_{HF}$, $P_{LF1}$ or $P_{LF2}$ is one of 30 values.

4. The method of claim 3, wherein each of the 30 values is an integer representing the sub-range of the power spectrum falling between each of the following numbers, in msec$^2$:
99999, 12000, 11000, 9000, 7800, 6400, 5200, 4200, 3200, 2500, 2100, 1700, 1300, 1000, 900, 820, 730, 640, 570, 490, 420, 360, 310, 255, 200, 145, 95, 55, 25, 15 and 0 for $P_{HF}$;
99999, 9000, 7800, 6400, 5200, 4200, 3400, 3000, 2600, 2200, 1850, 1550, 1300, 1100, 1000, 900, 810, 730, 640, 570, 490, 420, 350, 300, 250, 200, 150, 120, 70, 25 and 0 for $P_{LF1}$; and
99999, 9000, 7800, 6400, 5200, 4200, 3400, 3000, 2600, 2200, 1850, 1550, 1300, 1100, 1000, 900, 810, 730, 640, 570, 490, 420, 350, 300, 250, 200, 150, 120, 70, 25 and 0 for $P_{LF2}$.

5. The method of claim 1, further comprising replacing an artifactual parameter value with an interpolated parameter value prior to step (c).

6. The method of claim 1, wherein in step (c) the frequency domain analysis comprises reducing the value of a power in a lower frequency subrange if the total power in the subrange of 0.5 to 1.0Hz exceeds 3000ms$^2$.

7. The method of claim 1, wherein prior to step (b) the data are subjected to a data preparation algorithm.

8. The method of claim 1, wherein in step (c) the frequency domain analysis is performed via a power spectral analysis algorithm.

9. A system for characterizing autonomic nervous system activity of a patient comprising:
i) a processor; and
ii) a machine-readable medium tangibly embodying a program of instructions executable by the processor to perform the method of claim 1.

10. The system of claim 9, further comprising a display means to present results to a user thereof via a computer interface.

11. A computer-readable medium tangibly embodying a program of instructions executable by a computer to perform a method for characterizing autonomic nervous system activity of a patient which method comprises:
(a) acquiring electrocardiographic data from the patient with an electrocardiographic device;
(b) determining from the electrocardiographic data obtained in step (a) a plurality of time intervals between successive R-waves;
(c) analyzing the plurality of time intervals by frequency domain analysis so as to quantitate the following parameters:
i) power of high frequency ($P_{HF}$);
ii) power of low frequency 1 ($P_{LF1}$) (0.07 to 0.15 Hz);
iii) power of low frequency 2 ($P_{LF2}$) (0.033 to 0.07 Hz);
iv) difference between power of low frequency 1 and high frequency ($P_{LF1} -_{LF1} P_{HF}$);
v) maximum amplitude of spectral function in a low frequency band ($S_{LFmax}$);
vi) frequency at a point of maximum amplitude of spectral function in the low frequency band ($F_{LFmax}$);
vii) maximum amplitude of spectral function in a high frequency band ($S_{HFmax}$);
viii) frequency at a point of maximum amplitude of spectral function in the high frequency band ($F_{HFmax}$);
ix) ratio of power of high frequency to power of low frequency 1, ($P_{HF}/P_{LF1}$);
x) ratio of power of high frequency to power of low frequency (sum of powers of low frequency 1 and low frequency 2), ($P_{HF}/(P_{LF1} + P_{LF2})$);
xi) heart rate (HR);
and, if a spectral peak falls in the range of a middle frequency band,
xii ($S_{MF}$) maximum amplitude of spectral function in a middle frequency band; and
(d) applying a clusterization algorithm to the parameter values quantitated in step (c) so as to determine two further parameters, one of which correlates with sympathetic nervous system activity and the other of which correlates with parasympathetic nervous system activity, wherein parasympathetic nervous system activity is determined by applying the clusterization algorithm to parameters (c)(i) to (c)(iv) and wherein sympathetic nervous system activity is determined by applying the clusterization algorithm to parameters (c) (ii) , (c) (iii) , and (c) (v) to (c)(xii).

* * * * *